(12) United States Patent
Corl

(10) Patent No.: US 10,575,815 B2
(45) Date of Patent: Mar. 3, 2020

(54) INTRAVASCULAR ULTRASOUND IMAGING APPARATUS, INTERFACE ARCHITECTURE, AND METHOD OF MANUFACTURING

(71) Applicant: VOLCANO CORPORATION, San Diego, CA (US)

(72) Inventor: Paul Douglas Corl, Palo Alto, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 37 days.

(21) Appl. No.: 15/617,513

(22) Filed: Jun. 8, 2017

(65) Prior Publication Data
US 2017/0265842 A1 Sep. 21, 2017

Related U.S. Application Data

(63) Continuation of application No. 15/611,084, filed on Jun. 1, 2017, which is a continuation of application No. 14/137,269, filed on Dec. 20, 2013.
(Continued)

(30) Foreign Application Priority Data

Jul. 3, 2014 (WO) ................ 2014105725

(51) Int. Cl.
*A61B 8/12* (2006.01)
*A61B 8/08* (2006.01)
(Continued)

(52) U.S. Cl.
CPC .............. *A61B 8/12* (2013.01); *A61B 8/0891* (2013.01); *A61B 8/4483* (2013.01);
(Continued)

(58) Field of Classification Search
CPC ....... A61B 8/12; A61B 8/0891; A61B 8/4483; B06B 2201/76; B06B 1/0207; B06B 1/0633
See application file for complete search history.

(56) References Cited

U.S. PATENT DOCUMENTS

| 4,398,116 A * | 8/1983 | Lewis ................... B06B 1/0625 310/334 |
| 4,917,097 A * | 4/1990 | Proudian .................. A61B 8/12 600/463 |

(Continued)

FOREIGN PATENT DOCUMENTS

| GB | 2315020 | 1/1998 |
| WO | 9723865 A1 | 7/1997 |

OTHER PUBLICATIONS

International Search Report and Written Opinion received in corresponding PCT Application No. PCT/US2013/077044 dated Apr. 16, 2014.
(Continued)

*Primary Examiner* — Oommen Jacob

(57) ABSTRACT

Sold-state intravascular ultrasound (IVUS) imaging devices, systems, and methods are provided. Some embodiments of the present disclosure are particularly directed to compact and efficient circuit architectures and electrical interfaces for an ultrasound transducer array used in a solid-state IVUS system. In one embodiment, an intravascular ultrasound (IVUS) device includes: a flexible elongate member; an ultrasound scanner assembly disposed at a distal portion of the flexible elongate member, the ultrasound scanner assembly including an ultrasound transducer array; an interface coupler disposed at a proximal portion of the flexible elongate member; and a cable disposed within and extending along a length of the flexible elongate member between the ultrasound scanner assembly and the interface coupler. The
(Continued)

cable includes four conductors electrically coupling the ultrasound scanner assembly and the interface coupler.

20 Claims, 14 Drawing Sheets

Related U.S. Application Data

(60) Provisional application No. 61/746,804, filed on Dec. 28, 2012.

(51) Int. Cl.
*A61B 8/00* (2006.01)
*B06B 1/02* (2006.01)
*B06B 1/06* (2006.01)

(52) U.S. Cl.
CPC .......... *B06B 1/0207* (2013.01); *B06B 1/0633* (2013.01); *B06B 2201/76* (2013.01)

(56) References Cited

U.S. PATENT DOCUMENTS

| | | |
|---|---|---|
| 5,567,653 A | 10/1996 | Bertin et al. |
| 5,924,993 A | 7/1999 | Hadjicostis et al. |
| 6,261,249 B1* | 7/2001 | Talish .................. A61B 8/4227 600/459 |
| 6,283,921 B1 | 9/2001 | Nix et al. |
| 6,641,540 B2 | 11/2003 | Fleischman et al. |
| 6,776,763 B2 | 8/2004 | Nix et al. |
| 7,226,418 B2 | 6/2007 | Kim |
| 7,384,128 B2 | 6/2008 | Sheahan et al. |
| 7,846,101 B2 | 12/2010 | Eberle et al. |
| 8,485,974 B2 | 7/2013 | Liu et al. |
| 2003/0018261 A1* | 1/2003 | Bae .................... G01S 7/52025 600/447 |
| 2003/0208119 A1 | 11/2003 | Crowley |
| 2006/0052707 A1* | 3/2006 | Dickinson ................ A61B 8/12 600/466 |
| 2006/0058655 A1* | 3/2006 | Little ...................... A61B 8/00 600/437 |
| 2007/0112344 A1* | 5/2007 | Keilman ............... A61B 5/0031 606/41 |
| 2007/0239024 A1 | 10/2007 | Eberle et al. |
| 2009/0216125 A1* | 8/2009 | Lenker ..................... A61B 8/12 600/445 |
| 2009/0270737 A1 | 10/2009 | Thornton |
| 2010/0234736 A1 | 9/2010 | Corl |
| 2010/0280388 A1 | 11/2010 | Huang |
| 2011/0010925 A1* | 1/2011 | Nix .................... A61B 1/00082 29/594 |
| 2011/0034809 A1* | 2/2011 | Eberle .................. B06B 1/0633 600/467 |
| 2011/0087104 A1 | 4/2011 | Moore et al. |
| 2011/0237955 A1 | 9/2011 | Dietz et al. |
| 2011/0319762 A1* | 12/2011 | Lerman .................... A61B 8/06 600/443 |
| 2012/0235539 A1* | 9/2012 | Bibl ...................... B06B 1/0644 310/316.01 |
| 2013/0144165 A1 | 6/2013 | Ebbini et al. |
| 2013/0258814 A1* | 10/2013 | Rich ...................... H04R 17/00 367/157 |
| 2014/0318859 A1* | 10/2014 | Van Rens ............. H01B 7/048 174/70 R |
| 2017/0265842 A1* | 9/2017 | Corl ........................ A61B 8/12 |

OTHER PUBLICATIONS

International Searching Authority/European Patent Office, "Communication—The Supplementary European Search Report," for European Application No. 13867582.2, dated Jul. 15, 2016.

* cited by examiner

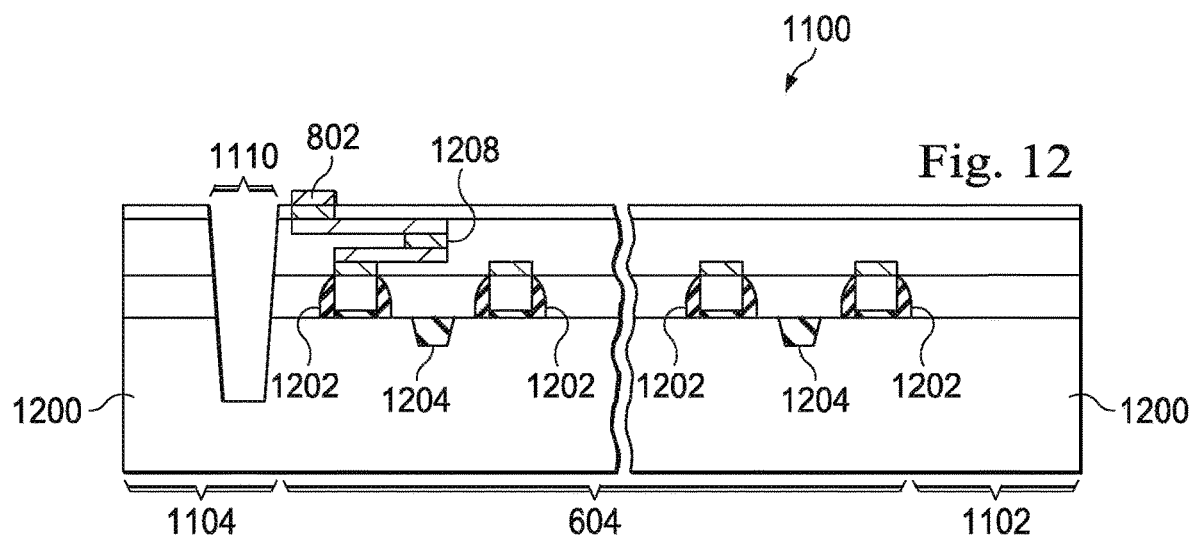
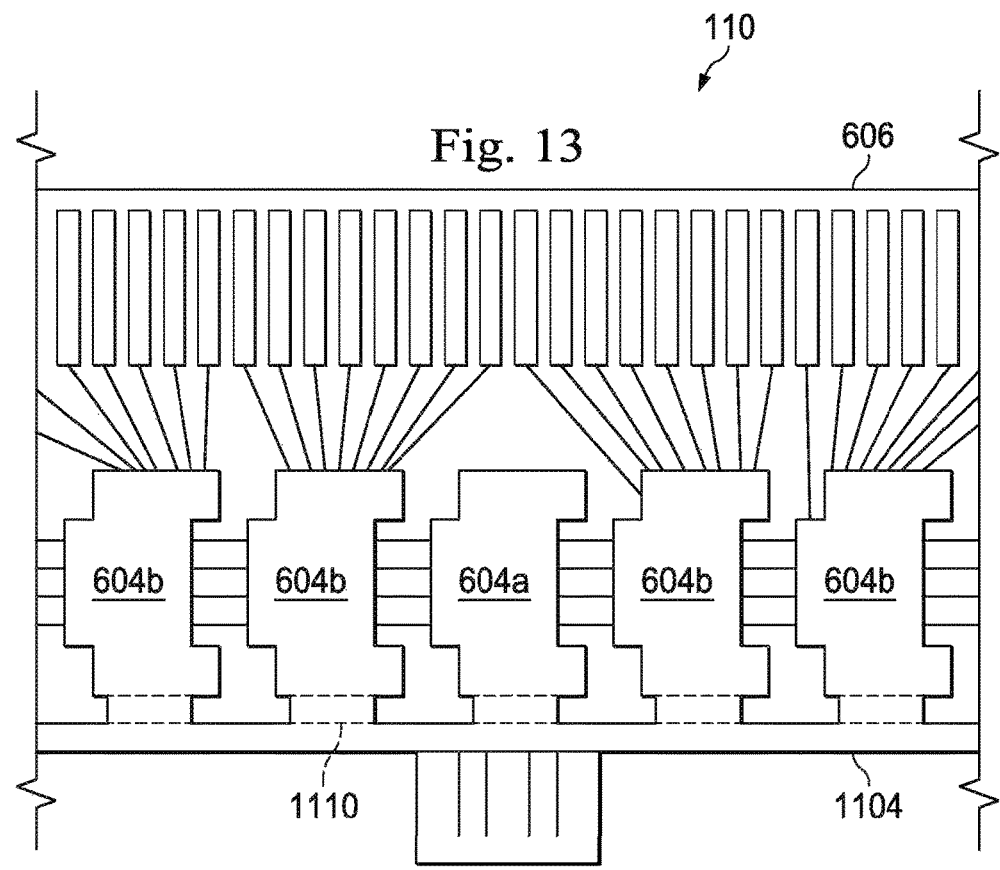

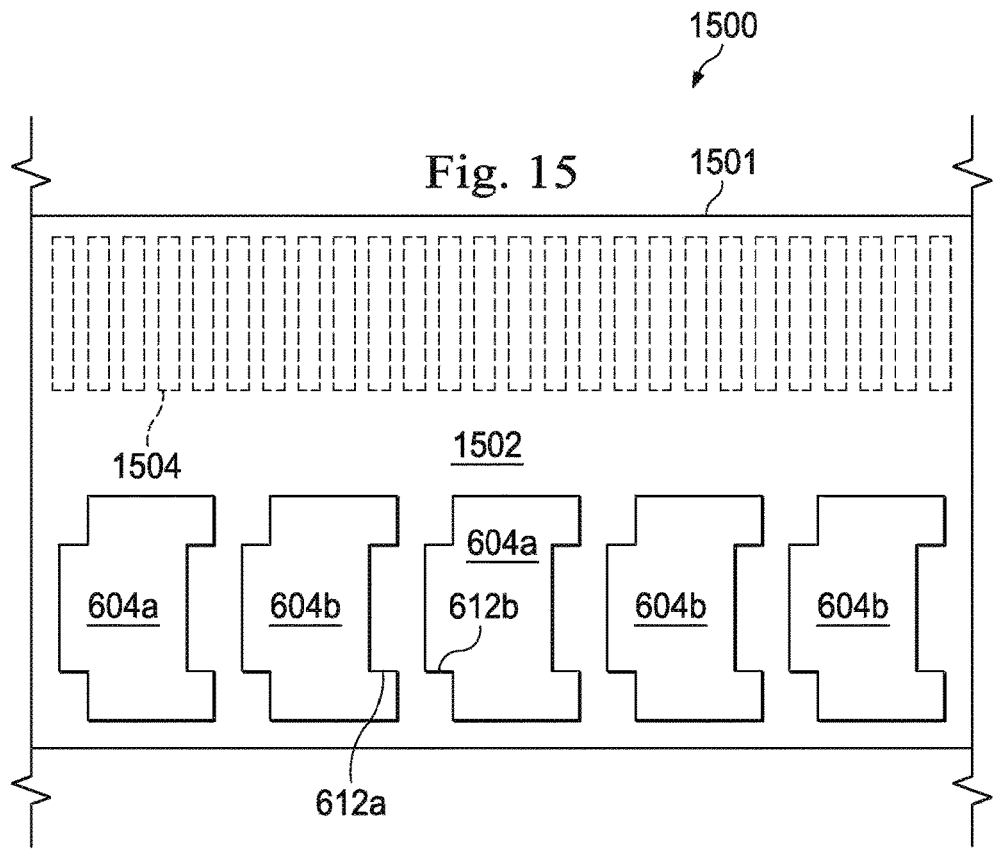
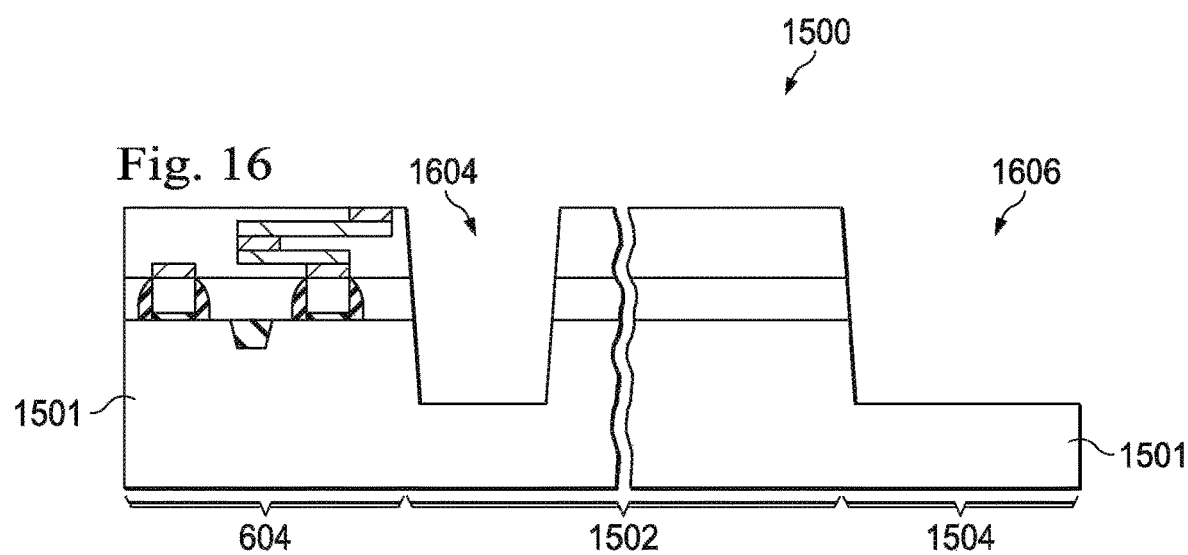

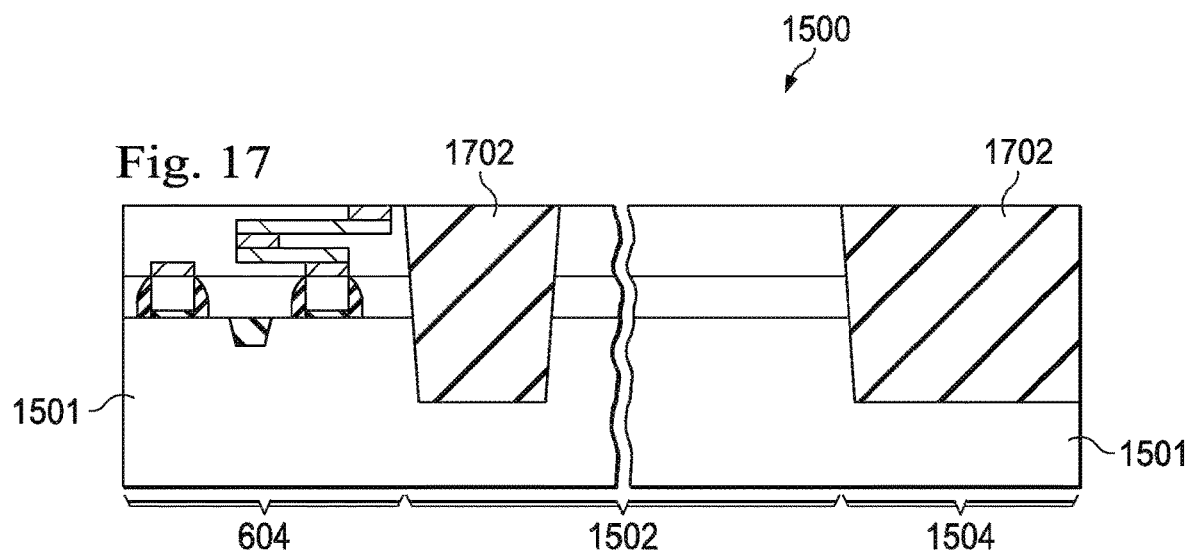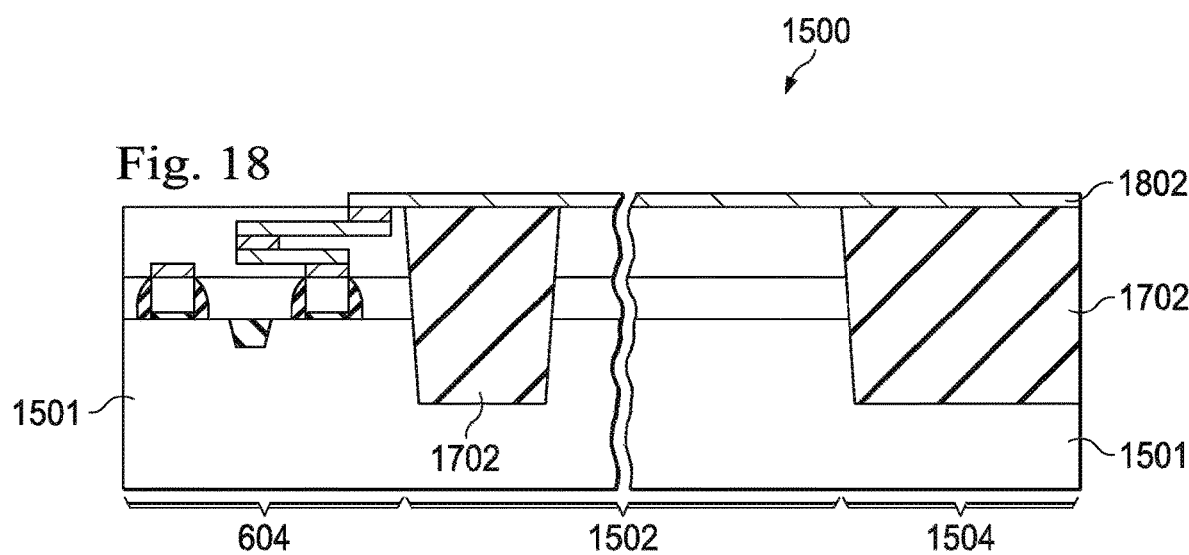

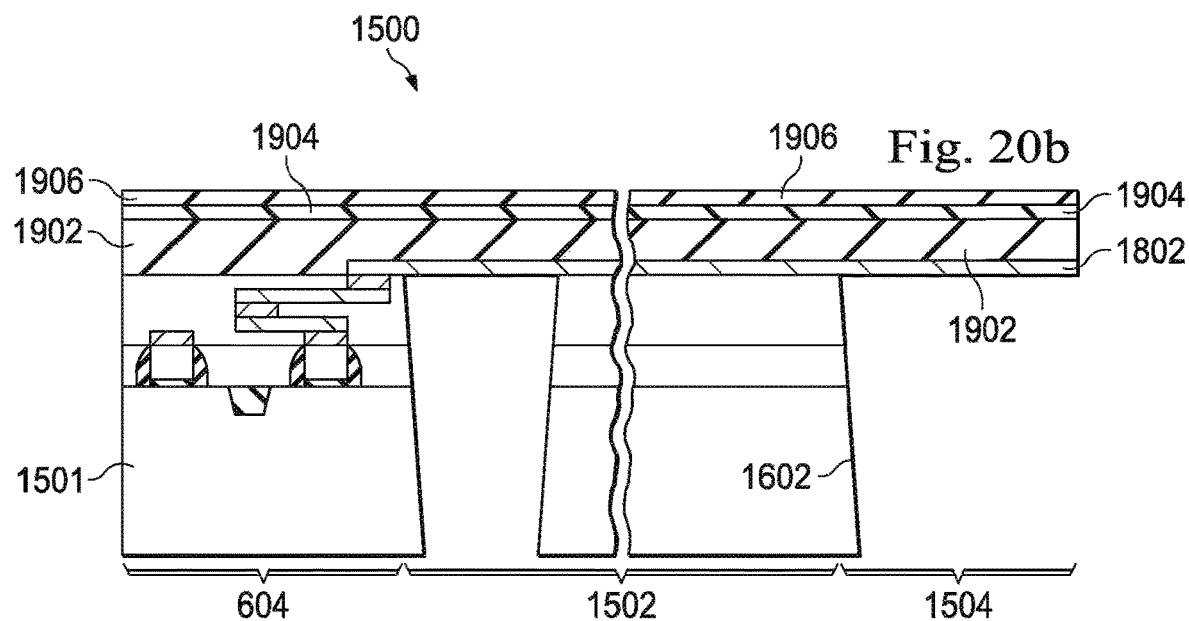
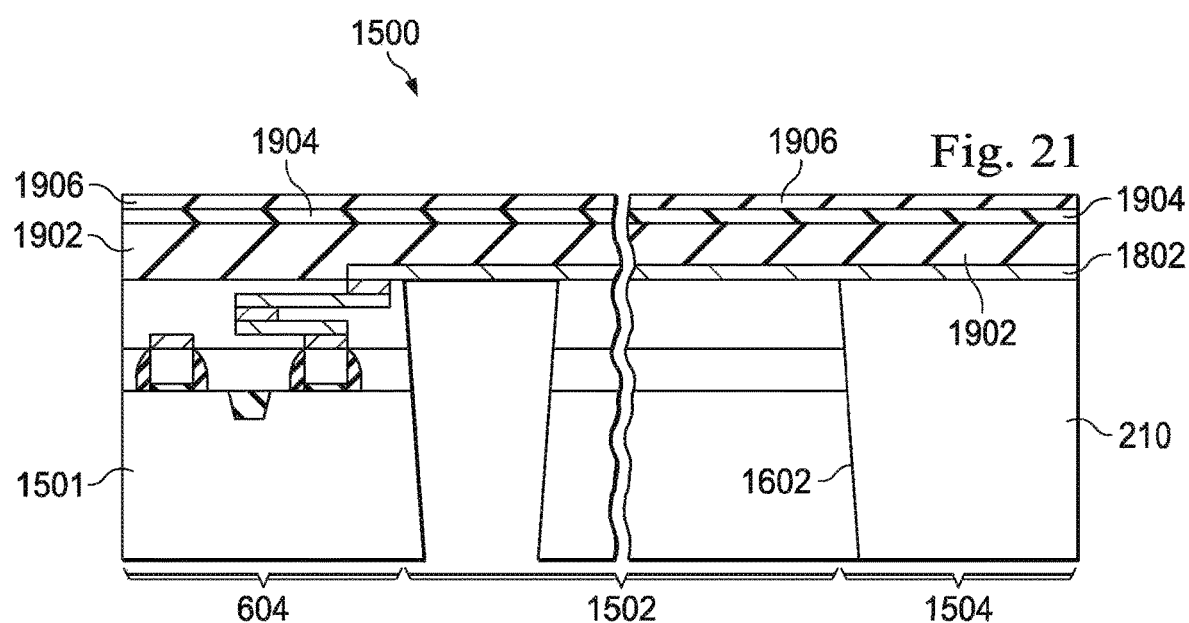

INTRAVASCULAR ULTRASOUND IMAGING APPARATUS, INTERFACE ARCHITECTURE, AND METHOD OF MANUFACTURING

CROSS-REFERENCE TO RELATED APPLICATIONS

The present application claims priority to and the benefit of U.S. Provisional Patent Application No. 61/746,804, filed Dec. 28, 2012, which is hereby incorporated by reference in its entirety.

TECHNICAL FIELD

The present disclosure relates generally to intravascular ultrasound (IVUS) imaging and, in particular, to a solid-state IVUS imaging system. In various embodiments, the IVUS imaging system includes an array of ultrasound transducers, such as piezoelectric zirconate transducers (PZTs), capacitive micromachined ultrasonic transducers (CMUTs), and/or piezoelectric micromachined ultrasound transducers (PMUTs), controlled by transmit/receive interface controllers. For example, some embodiments of the present disclosure provide an IVUS imaging system including transmit/receive interface controllers particularly suited to imaging a human blood vessel.

BACKGROUND

Intravascular ultrasound (IVUS) imaging is widely used in interventional cardiology as a diagnostic tool for a diseased vessel, such as an artery, within the human body to determine the need for treatment, to guide the intervention, and/or to assess its effectiveness. To perform IVUS imaging study, an IVUS catheter that incorporates one or more ultrasound transducers is passed into the vessel and guided to the area to be imaged. The transducers emit and receive ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by a transducer and passed along to an IVUS imaging system, which is connected to the IVUS catheter by way of a patient interface module (PIM). The imaging system processes the received ultrasound signals to produce a cross-sectional image of the vessel where the device is placed.

There are two types of IVUS catheters commonly in use today: rotational and solid-state. For a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning, echoes reflected from various tissue structures. The IVUS imaging system assembles a two dimensional display of the vessel cross-section from a sequence of pulse/acquisition cycles occurring during a single revolution of the transducer.

In contrast, solid-state IVUS catheters carry an ultrasound scanner assembly that includes an array of ultrasound transducers distributed around the circumference of the device connected to a set of transducer control circuits. The transducer control circuits select individual transducers for transmitting an ultrasound pulse and for receiving the echo signal. By stepping through a sequence of transmitter-receiver pairs, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-gate scanner can be wired directly to the imaging system with a simple electrical cable and a standard detachable electrical connector.

One factor in IVUS catheter performance is catheter agility. Rotational catheters tend to smoothly advance around corners due to the flexible rotating drive shaft contained within the sheath. However, rotational catheters often require a long rapid exchange tip to engage the guidewire, and the long tip may limit the advance of the imaging core containing the transducer. For example, this may prevent the catheter from being advanced to very distal locations within the coronary arteries. On the other hand, solid-state IVUS catheters may have a shorter tip as the guidewire can pass through the interior lumen of the scanner. However, some solid-state designs have rigid segments that limit the ability to advance the catheter around sharp bends in the vasculature. Solid-state IVUS catheters also tend to be larger in diameter than rotational catheters to accommodate the transducer array and the associated electronics.

While existing IVUS imaging systems have proved useful, there remains a need for improvements in the design of the solid-state scanner to reduce its overall diameter and to reduce the length of rigid portions of the catheter in order to provide improved access to the vasculature. Such improvements may maintain or even improve the imaging performance of the system. Accordingly, the need exists for improvements to the transducer structures, to the electrical interface, to the IVUS scanner, to the IVUS catheter, and to the overall IVUS system, as well as to the methods used in manufacturing.

SUMMARY

Embodiments of the present disclosure provide a compact and efficient ultrasound scanner assembly and an adaptable electrical interface unit in a solid-state intravascular ultrasound imaging system.

In some embodiments, an intravascular ultrasound (IVUS) device is provided. The device comprises: a flexible elongate member; an ultrasound scanner assembly disposed at a distal portion of the flexible elongate member, the ultrasound scanner assembly including an ultrasound transducer array; an interface coupler disposed at a proximal portion of the flexible elongate member; and a cable disposed within and extending along a length of the flexible elongate member between the ultrasound scanner assembly and the interface coupler, the cable including four conductors electrically coupling the ultrasound scanner assembly and the interface coupler.

In some embodiments, an intravascular ultrasound (IVUS) device is provided. The device comprises: a flexible elongate member; a patient interface module (PIM) coupler coupled to a proximal portion of the flexible elongate member; an array of ultrasound transducers coupled to a distal portion of the flexible elongate member; a transducer control circuit electrically coupled to the array of ultrasound transducers; and a cable disposed within and extending along a length of the flexible elongate member between the connector and the transducer control circuit, the cable including four conductors electrically coupling the transducer control circuit and the connector.

In some embodiments, an intravascular ultrasound (IVUS) device is provided. The devices comprises: a flexible elongate member; a patient interface module (PIM) coupler disposed at a proximal portion of the flexible elongate member; an ultrasound scanner assembly disposed at a distal portion of the flexible elongate member; and a cable disposed within and extending along a length of the flexible elongate member between the ultrasound scanner assembly and the interface coupler, the cable including four conductors electrically coupling the ultrasound scanner assembly and the interface coupler, wherein the ultrasound scanner assembly includes: a controller portion including a plurality of transducer control circuits, the controller portion disposed adjacent a proximal portion of the ultrasound scanner assembly; a transducer portion including a plurality of ultrasound transducers, the transducer portion disposed adjacent a distal portion of the ultrasound scanner assembly; an a transition portion disposed between the controller portion and the transducer portion.

In some embodiments, an ultrasound scanner assembly is provided. The scanner assembly comprises a substrate; a plurality of ultrasound transducers disposed on the substrate in an annular configuration; and a plurality of transducer control circuits disposed on the substrate, wherein a transducer control circuit of the plurality of transducer control circuits includes a first edge configured to interface with a second edge of an adjacent transducer control circuit of the plurality of transducer control circuits.

In some embodiments, a method of manufacturing an ultrasound scanner assembly is provided. The method comprises: providing a super-die including a first controller, a second controller, and a support member extending between and connecting the first and second controllers; securing the first and second controllers to a circuit substrate; and removing the support member from the first and second controllers after the securing of the first and second controllers to the circuit substrate.

In some embodiments, a method of manufacturing an intravascular ultrasound (IVUS) device is provided. The method comprises: providing a semiconductor device having a controller, a sacrificial region, and a reserved region; removing a portion of the sacrificial region to define one or more recessed sections; introducing a resilient material into the one or more recessed sections; forming a circuit structure on the semiconductor device, the circuit structure contacting the resilient material and the controller such that the controller is electrically coupled to the circuit structure; removing the resilient material from the circuit structure; and attaching an ultrasound transducer to the circuit structure.

In some embodiments, a method of ultrasound imaging is provided. The method comprises: placing a guide wire a vascular structure; advancing an intravascular ultrasonic (IVUS) device over the guide wire, the IVUS catheter including an ultrasound transducer array; operating the IVUS catheter utilizing a four-lead interface, the operating performed to cause a transducer of the ultrasound transducer array to emit an ultrasonic waveform; generating echo data by the IVUS catheter based on a reflected echo of the ultrasonic waveform; providing the echo data to an IVUS console utilizing the four-lead interface; and processing the echo data for display.

In some embodiments, a method of interfacing with an intravascular ultrasonic (IVUS) device having a four-line interface and an ultrasound transducer is provided. The method comprises: transmitting a first signal via a first pair of lines of the four-line interface, the first signal configuring a mode of operation for the IVUS catheter; transmitting a second signal via the first pair of lines, the second signal triggering the transducer to emit an ultrasonic waveform and to receive a reflected echo of the ultrasonic waveform; receiving echo data based on the reflected echo via the first pair of lines.

Some embodiments of the present disclosure utilize an interface architecture that provides control of the ultrasound mechanism and amplification of the received signals with a reduced set of signal lines connecting the scanner to the PIM and console. By reducing the number of signal lines, the diameter of the cable carrying the signals can be decreased, which may allow a corresponding decrease, in the diameter of the catheter body. Reducing the number of conductors also reduces the size of the junction between the cable and the scanner, thereby facilitating a reduced profile for improves access to small vessels. Furthermore, reducing the number of conductors may also allow the use of larger gauge conductors in the cable, which can improve device durability and reduce signal degradation. An enhanced serial communication scheme also provides flexibility and advanced features without adding additional conductors to the four-lead cable between the PIM and the transducer. Further embodiments of the present disclosure also provide cable impedance matching. In this way, the interface architecture supports balanced transmission lines, with each transmission line properly terminated to minimize reflections and distortion of the frequency response that can cause artifacts or degradation in the image.

Some embodiments of the present disclosure arrange the control wiring to reduce crosstalk, coupling, and other transmission line effects. For example, a four-conductor cable can be arranged in a "star quad" configuration with diagonal conductor pairs forming independent transmission lines. In this configuration, interference, line loss, and coupling between diagonal signal pairs is minimized by the symmetry of their placement. Embodiments of the present disclosure also arrange the control wiring to serve as a balanced differential pair. The balanced pair inhibits sensitivity to electro-magnetic interference (EMI), as well as reduces the susceptibility of the system to external interference from other devices. In some embodiments, the four-conductor interface cable incorporates a ground shield to further suppress EMI and susceptibility to external interference.

Embodiments of the present disclosure leverage an improved circuit design as well as an improved electrical interface to reduce the size of the scanner assembly. As the scanner assembly is rigid, decreasing the length creates a more responsive device. The length of the scanner is determined in part by the size and shape of the controllers as well as the need for a transition zone to accommodate differences in thee cross-sectional shapes of the transducer region and the controller region of the scanner. In some embodiments utilizing 8, 9, 16, or more transducer control circuits, the cross-sectional shape of the controller region more closely approximates the nearly circular cross-sectional shape of the transducer region. This permits a shorter transition zone between the two regions and a shorter overall scanner length. The resulting device is more flexible and, therefore, able to maneuver through complicated vascular branches.

Some embodiments utilize a super-die manufacturing configuration for the control circuitry. Multiple dies comprising the scanner control circuitry are manufactured as a single super-die that incorporates the multiple dies on a single substrate. The dies can then later be freed from the super-die. For example, the dies may be divided after they have been attached to a flexible circuit substrate. The super-die may contain a removable support structure that maintains a precise spacing and orientation of an array of devices such as transducer control circuits. This improves placement accuracy during assembly and enables the use of automated manufacturing tools instead of hand assembly. Likewise, the increased precision allows the use of smaller components. Furthermore, assembling multiple controllers as a group saves assembly time.

Additional embodiments utilize a microfabrication process to form a circuit structure on a semiconductor wafer used to manufacture transducer components. Forming the circuit structure on the wafer allows the use of precise semiconductor techniques resulting in more uniform connections and dramatically fewer alignment issues. It also eliminates the need to align and mount the semiconductor devices on a flex circuit. Instead once released from wafer, the pliable substrate takes the place of a flex circuit. In one such embodiment, remaining segments of the wafer are used to align any additional devices to be joined to the pliable substrate.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 12 is a simplified cross-sectional view of a super-die taken along an axis indicated in FIG. 11 according to an embodiment of the present design.

FIG. 13 is a top view of a portion of an ultrasound scanner assembly in a stage of manufacturing according to an embodiment of the present disclosure.

FIG. 15 is a top view of a portion of a semiconductor device in a stage of microassembly according to an embodiment of the present disclosure.

FIGS. 16-22 are simplified cross-sectional side views of a semiconductor device in various stages of a method of microassembly according to an embodiment of the present disclosure.

In particular, FIG. 16 is a cross-sectional side view of a semiconductor device in a stage of a method according to an embodiment of the present disclosure.

FIG. 17 is a cross-sectional side view of a semiconductor device similar to that of FIG. 16 showing a resilient material filling etched areas of a substrate.

FIG. 18 is a cross-sectional side view of a semiconductor device similar to that of FIG. 17 having interconnects formed on a substrate.

FIG. 19 is a cross-sectional side view of a semiconductor device similar to that of FIG. 18 showing a pliable film formed on a set of interconnects.

FIG. 20b is a cross-sectional side view of a semiconductor device similar to that of FIG. 20a showing a substrate after removing a resilient material.

FIG. 21 is a cross-sectional side view of a semiconductor device similar to that of FIG. 20b where an ultrasound scanner assembly includes an ultrasound transducer.

FIG. 22 is a cross-sectional side view of a semiconductor device similar to that of FIG. 21 after removing areas of attached substrate.

DETAILED DESCRIPTION

Figure 1:
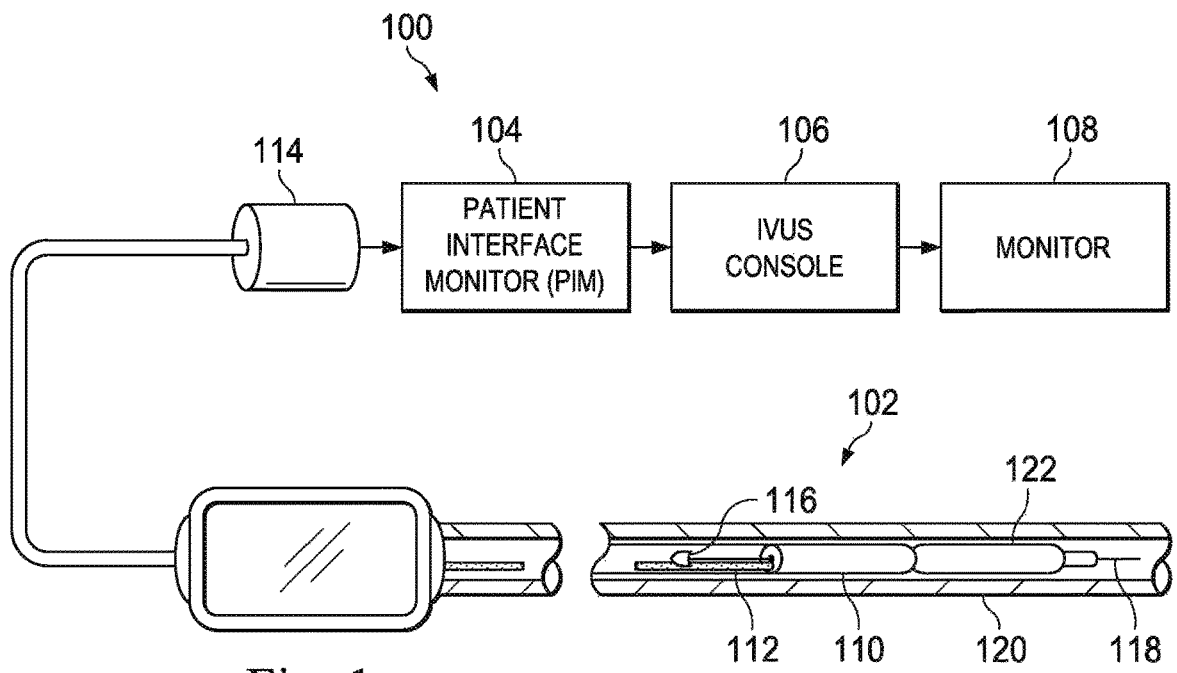
FIG. 1 is a diagrammatic schematic vim of an imaging system according to embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the IVUS system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intravascular ultrasound (IVUS) imaging system 100 according to an embodiment of the present disclosure. In some embodiments of the present disclosure, the IVUS imaging system 100 is a piezoelectric zirconate transducer (PZ) solid-state IVUS imaging system. In some embodiments, the system 100 incorporates capacitive micromachined ultrasonic transducers (CMUTs), and/or piezoelectric micromachined ultrasound transducers (PMUTs). The IVUS imaging system 100 may include an IVUS catheter 102, a patient interface module (PIM) 104, an IVUS console or processing system 106, and/or a monitor 108.

At a high level, the IVUS catheter 102 emits ultrasonic energy from a scanner assembly 110 at the tip of the device. The ultrasonic energy is reflected by tissue structures surrounding the scanner 110 and the echo signals from the tissue are received and amplified by the scanner 110.

The PIM 104 facilitates communication of signals between the IVUS console 106 and the IVUS catheter 102 to control the operation of the scanner assembly 110. This includes generating control signals to configure the scanner and trigger the transmitter circuits and transferring echo signals captured by the scanner assembly 110 to the IUVS console 106. With regard to the echo signals, the PIM 104 forwards the received signals and, in some embodiments, performs preliminary signal processing prior to transmitting the signals to the console 106. In examples of such embodiments, the PIM 104 performs amplification, filtering, and/or aggregating of the data. In an embodiment, the PIM 104 also supplies high- and low-voltage DC power to support operation of the circuitry within the scanner 110.

The IVUS console 106 receives the echo data from the scanner 110 by way of the PIM 104 and processes the data to create an image of the tissue surrounding the scanner 110. The console 106 may also display the image on the monitor 108.

In some embodiments, the IVUS catheter includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS catheter 102 includes the ultrasound scanner assembly 110 at a distal end of the device 102 and a cable 112 extending along the longitudinal body of the device 102. The cable 112 terminates in a connector 114 at a proximal end of the device 102. The connector 114 electrically couples the cable 112 to the PIM 104 and physically couples the IVUS catheter 102 to the PIM 104. In an embodiment, the IVUS catheter 102 further includes a guide wire exit port 116. Accordingly, in some instances the IVUS catheter is a rapid-exchange catheter. The guide wire exit port 116 allows a guide wire 118 to be inserted towards the distal end in order to direct the device 102 through a vessel 120. Vessel 120 represents fluid filled or surrounded structures, both natural and man-made, within a living body that may be imaged and can include for example, but without limitation, structures such as: organs including, the liver, heart, kidneys, gall bladder, pancreas, lungs; ducts; intestines; nervous system structures including the brain, dural sac, spinal cord and peripheral nerves; the urinary tract; as well as valves within the blood or other systems of the body. In addition to imaging natural structures, the images may include imaging manmade structures such as, but without limitation, heart valves, stents, shunts, filters and ether devices positioned within the body. In an embodiment, the IVUS catheter 102 also includes an inflatable balloon portion 122 near the distal tip. The balloon portion 122 is open to a lumen that travels along the length of the IVUS catheter and ends in an inflation port (not shown). The balloon 122 may be selectively inflated and deflated via the inflation port.

The IVUS catheter 102 is designed to provide high-resolution imaging from within narrow passageways. To advance the performance of IVUS imaging devices compared to the current state of the art, embodiments of the present disclosure incorporate advanced transducer technologies, such as PMUT, that offer wide bandwidth (>100%). The broad bandwidth is important for producing a short ultrasound pulse to achieve optimum resolution in the radial direction. The improved resolution provided by PMUT and other advanced ultrasound transducer technologies facilitates better diagnostic accuracy, enhances the ability to discern different tissue types, and enhances the ability to accurately ascertain the borders of the vessel lumen. Embodiments of the present disclosure also have improved flexibility and reduced diameter allowing greater maneuverability and leading to increased patient safety and comfort. Specific embodiments also provide faster, more accurate, and less expensive methods of manufacturing the device 102.

Figure 2:
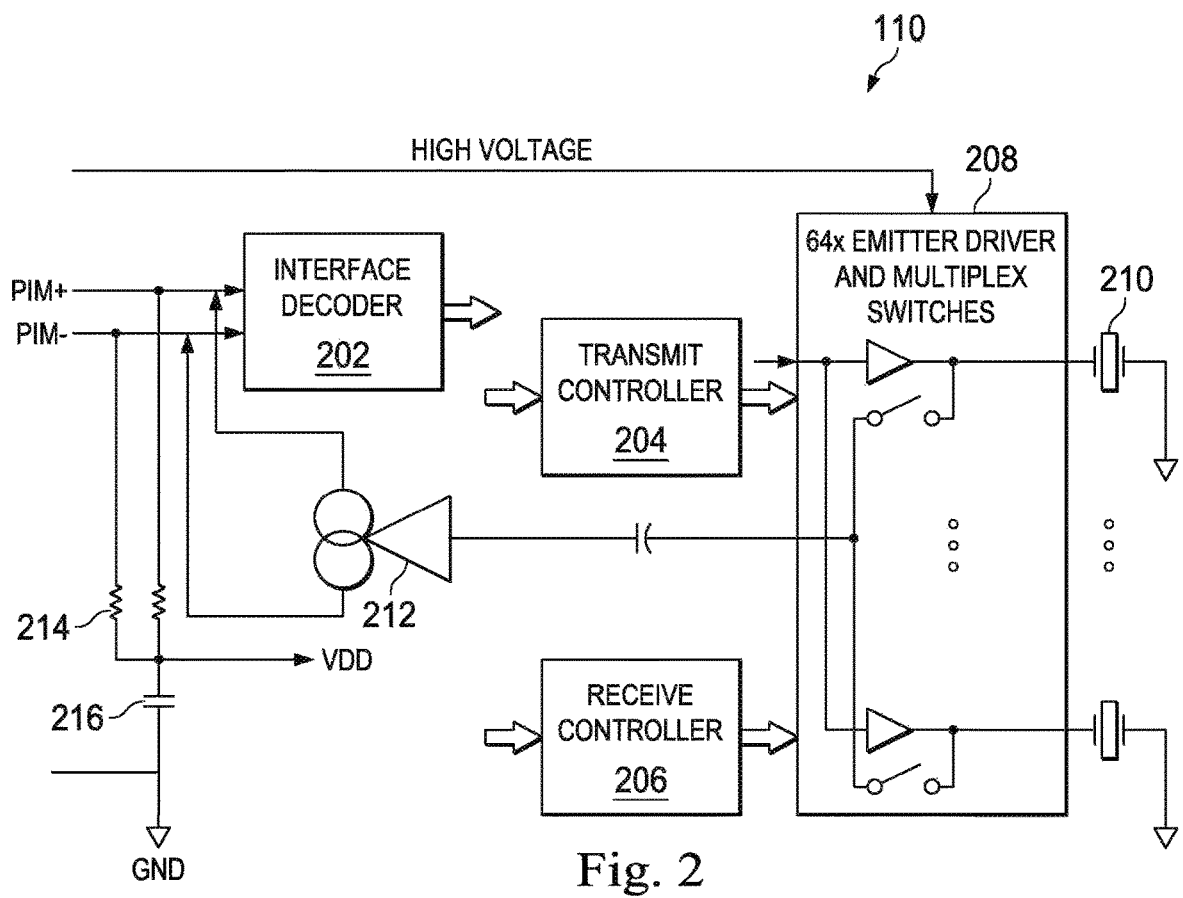
FIG. 2 is a simplified schematic illustration of an ultrasound scanner assembly according to an embodiment of the present disclosure.

FIG. 2 is a simplified schematic illustration of an ultrasound scanner assembly 110 according to an embodiment of the present disclosure. In contrast to conventional designs, this embodiment provides an improved transducer interface that requires fewer signal lines, thereby reducing the number of conductors needed to operate the transducers. The scanner 110 includes six major blocks, the interface decoder 202, the transmit controller 204, the receive controller 206, the driver and multiplexer array 208, the ultrasound transducers 210, and the echo amplifier 212. In physical implementations, any of the major blocks of the scanner 110 may be divided among one or more separate integrated circuit chips.

The scanner 110 receives four inputs. A High Voltage signal supplies DC voltage to the high power driver circuits that power the ultrasound transducers 210 when in transmit mode. A GND signal provides a common ground for the scanner circuitry. The remaining inputs, PIM+ and PIM−, are a differential pair of bidirectional multipurpose signals. In some implementations, the PIM+/− signal pair is used to: (1) supply low-voltage DC power ($V_{dd}$) to drive the circuitry of the scanner 110, (2) operate as a serial communication channel to permit the configuration of the transmit controller 204, the receive controller 206, and the multiplexer array 208, (3) operate as a serial communication channel to support advanced features such as programmability and status reporting, (4) carry the transmit trigger pulses as a balanced differential signal from the PIM 104 to activate the transmitter and timing circuitry included on the scanner, and (5) conduct the balanced output signal from the echo amplifier 212 to the PIM 104.

In order to supply an operating voltage, the PIM+/− differential pair maintains a substantially constant common mode offset voltage relative to ground (GND) as described by the equation:

$$V_{dd}(V_{PIM+}+V_{PIM-})/2$$

$V_{dd}$ is the voltage supplied to power the low-voltage circuitry scanner 110, which includes circuitry other than the power transmit drivers, $V_{PIM+}$ is the voltage of the PIM+ input, and $V_{PIM-}$ is the voltage of the PIM− input. In sore instances, $V_{dd}$ is between about 1.2 V and about 5.0 V. In one example, $V_{dd}$ is 3.3V DC. By maintaining a constant offset voltage, the PIM+, pair can be used to power the circuitry of the scanner 110 while also serving the other functions described.

In order to carry data to the scanner, including the aforementioned configuration data, control data, and/or transmit triggers, the PIM+/− pair may utilize a three-state encoding. For example, the PIM+/− pair may be limited to three valid states, positive ($V_{PIM+}$=high, $V_{PIM-}$=low), negative ($V_{PIM+}$=low, $V_{PIM-}$=high) and idle ($V_{PIM+}$=$V_{PIM-}$≈$V_{dd}$). In some instances, the low state is defined as between 0V and $0.5 \times V_{dd}$, the high state is defined as between $1.5 \times V_{dd}$ and $2 \times V_{dd}$, and the idle state is defined as between $V_{dd}$ and $1.25 \times V_{dd}$. In an exemplary embodiment where $V_{dd}$=3.3V, each of the PIM+ and PIM− may have a peak-to-peak amplitude from 3.3V p-t-p to 6.6V p-t-p, or a differential voltage ranging from 6.6V to 13.2V. Commonly these signal amplitudes scale in proportion to the $V_{dd}$ supply voltage.

These high, low, and idle values are used to implement a serial data protocol. Because the PIM+/− pair does not necessarily have an associated clock, some embodiments make use of asynchronous serial protocols. Exemplary asynchronous protocols include Manchester code, return-to-zero (RZ), and asynchronous non-return-to-zero (NRZ). A range of bitrates contemplated for the PIM+/− pair between about 10 MHz and 60 MHz, with an exemplary bitrate of 20 MHz given. However, it is understood that other titrates are supported.

Accordingly, the serial data conveyed via the PIM+/− lines can be used to configure one or more aspects of the scanner 110 including, without limitation, the designated transmitting and receiving transducers, and the length, duration, frequency, and other characteristics of the emitted waveform. To do so, the interface decoder 202 may convert the three-state encoded PIM+/− signals into binary control signals for the transmit controller 204, the receive controller 206, and other associated circuitry.

In one example, configuration data received over via PIM+/− inputs selects transmitting and receiving transducers. The interface decoder 202 converts the three-state PIM+/− instruction into a binary value. In some embodiments incorporating addressable transmit and receive registers within the transmit controller 204 and receive controller 206, the binary value contains an address for the registers that enables one or more transducers. In this manner, the address contained within the binary value selects transmitting and receiving transducers for subsequent ultrasonic imaging. In some embodiments incorporating shift transmit and receive registers, the binary value shifts an active logic value through one or more of the registers in order to enable the designated transducers. In some such embodiments, the binary values correspond to clock, load, and shift direction inputs associated with each shift register.

Transmit triggers may also be received over the PIM+/− inputs. Transmit triggers initiate an ultrasonic transmission by activating one or more channels of driver circuits. In response, the drivers excite one or more selected transmit transducers causing the selected transducer(s) to produce an ultrasonic waveform. The waveform is reflected by the tissue and other structures near and around the scanner 110 creating ultrasonic echoes that are captured by one or more receiving transducers selected by multiplexer array 208.

In some embodiments, the PIM+/− pair transmits the echo signal captured by the designated receiving transducer(s) 210 from the scanner 110 to the PIM 104. The electrical signals generated by the selected receiving transducer from the echoes are routed by the multiplexer array 208 to the echo amplifier 212. In the illustrated embodiment, the echo amplifier 212 is a differential amplifier, although other amplifier types are contemplated. The outputs of the echo amplifier 212 are tied to the PIM+/− pair. To ensure the integrity of incoming signals on the PIM+/− lines, the echo amplifier 212 may have a high impedance differential current source output stage with output impedance much greater than the cable termination resistance 214. To avoid distortion of the echo data, the echo amplifier 212 inputs may have high input impedance as well. In some embodiments, the echo amplifier 212 need not produce a high voltage gain since ultrasound transducers 210 may be capable of generating a significant voltage when driving a high impedance load (such as the amplifier input). However, even with a voltage gain of 1, the amplifier provides a significant power gain (e.g. ~16 dB) due to the low (e.g. ~100Ω) characteristic impedance of the cable 112 extending along the length of the device 102.

The PIM+/− pair is terminated within the scanner 110 by a pair of resistors 214 that form a balanced differential termination to minimize cable reflections and distortion of the signals propagating over the cable 112. Typically, the total differential resistance matches the characteristic impedance of the cable 112. In some instances, the line resistance is in the range of 50-100Ω, with an exemplary resistance of approximately 75Ω. In some embodiments, the terminating resistance provided by the resistors 214 may be greater than the characteristic impedance of the cable. Such embodiments may rely on the PIM termination and cable losses to dampen ringing that may arise from the imperfect match to the cable characteristic impedance, while benefiting from the lower losses associated with the higher resistance of terminating resistors 214.

The resistors 214 may also be used in the generation of the $V_{dd}$ operating voltage. Accordingly, in some embodiments, the resistors 214 form a voltage divider. In the illustrated embodiment, the PIM+/− pair maintains a fixed differential offset voltage, as discussed above. The voltage divider produces a voltage equal to the midpoint of the PIM+/− pair and thereby supplies the operating voltage $V_{dd}$. To suppress voltage swings, in one such embodiment, the voltage divider includes a capacitor 216. An exemplary capacitor 216 is of the order of 100 pF.

Figure 3:
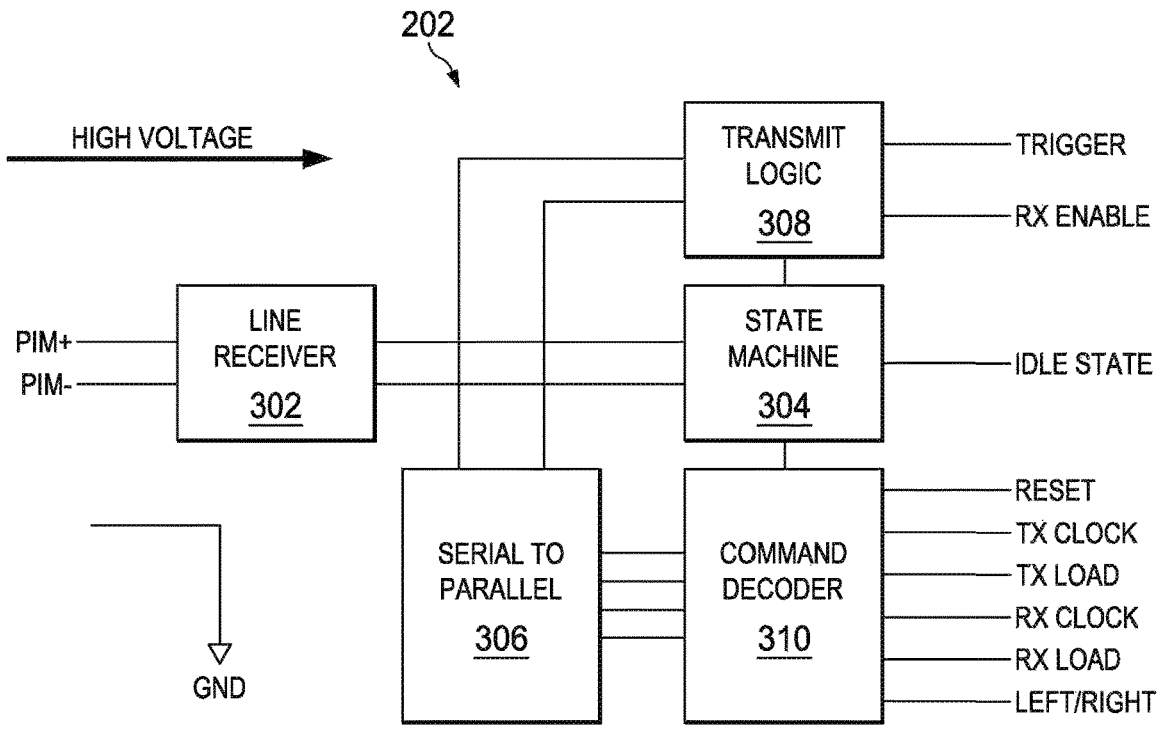
FIG. 3 is a simplified schematic illustration of an interface decoder according to an embodiment of the present disclosure.

FIG. 3 is a simplified schematic illustration of an interface decoder 202 according to an embodiment of the present disclosure. In some embodiments, the line receiver 302 translates the three-state PIM+/− differential signal pair into binary signals. In such embodiments, this includes rectifying hysteresis, debouncing, and/or filtering of the pair, and may further include translating the PIM+/− signals into an alternate voltage domain. The associated binary PIM values are then sent from the line receiver 302 to a state machine 304, a serial to parallel converter 306, and transmit logic 308. The state machine 304 determines whether the PIM+/− data indicates a command to configure the scanner assembly 110 and/or a transmit trigger, Note that, in some embodiments, the first bit of the data sequence determines whether the incoming data is a command or a transmit trigger. In alternate embodiments, all data sequences are treated as commands with a transmit trigger being a particular command within the command set.

For data sequences corresponding to configuration commands, the serial-to-parallel converter 306 parallelizes the serial PIM+/− data and provides it to the command decoder 310. The command decoder 310 then determines the corresponding control signal. Exemplary control signals include, without limitation, Reset, TX Clock, TX Load, RX Clock, RX Load, and Left/Right (shift control), For data sequences corresponding to transmit triggers, the state machine 304 enables the transmit logic 308. In response, the trasmit logic 308 drives one or more selected transducers to emit an ultrasonic waveform and activates one or more receiving transducers.

Figure 4:
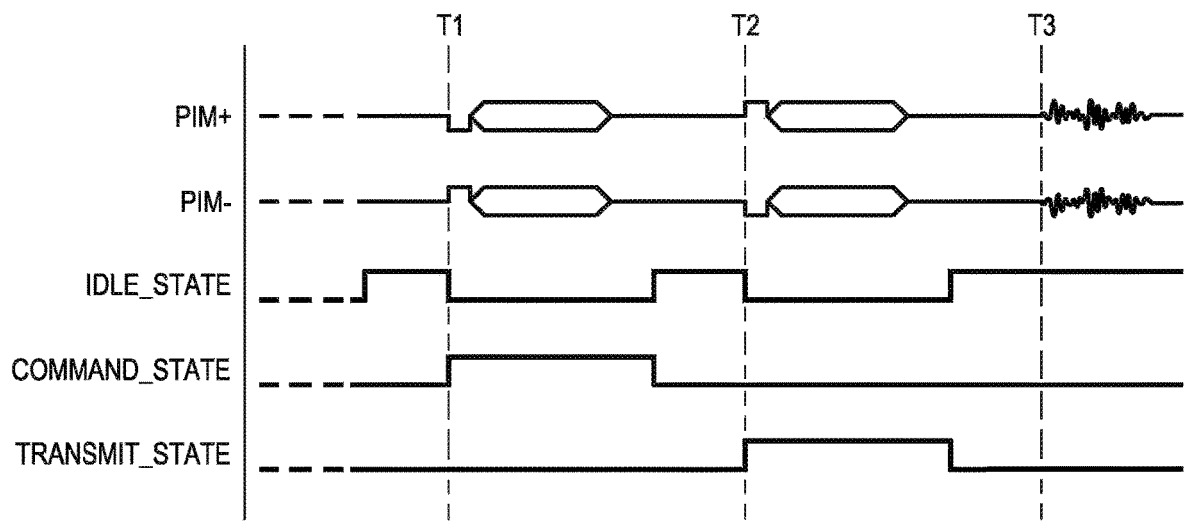
FIG. 4 is a timing diagram of are exemplary protocol for transmitting data to an ultrasound scanner assembly utilizing a PIM+/− pair according to an embodiment of the present disclosure.

FIG. 4 is a timing diagram of exemplary protocol for transmitting data to a scanner utilizing a PIM+/− pair a cording to an embodiment of the present disclosure n the exemplary protocol illustrated, the scanner 110 begins in an idle state, as indicated by the signal IDLE_STATE, IDLE_STATE, COMMAND_STATE, and TRANSMIT_STATE are signals internal to the state machine 304 representing three distinct operating states.

In the exemplary protocol, a command is indicated by transmitting a negative value aria the PIM+/− pair ($V_{PIM+}$=low, $V_{PIM-}$=high). Such a command instruction is illustrated beginning at time T1. The initial negative state directs the state machine 304 to transition from IDLE_STATE to COMMAND_STATE. Thereafter, the subsequent sequence of values of the PIM+/− pair are treated as a command code specifying and issuing a configuration command. An exemplary command code is 4 bits long, although command codes of any length are supported. Command codes may be used to define the active transmitter and receiver pair, to determine waveform characteristics for the ultrasonic emission, and/or to configure other device behavior. After transmission of the command code, the PIM+/− pair returns to idle. The state machine 304 times out after a period of time substantially larger than the data rate, for example 1.0 μsec, and returns to the IDLE_STATE. This time-out function may help to maintain synchronization during startup or in the event of a transient.

In the exemplary protocol, a trigger instruction to emit an ultrasonic waveform is issued by transmitting a positive value on the PIM+/− pair ($V_{PIM+}$=high, $V_{PIM-}$=low). An exemplary command instruction is illustrated beginning at time T2. The trigger instruction may include a sequence of trigger pulses that define the pulse width and number for cycles for the transmit burst. After the PIM+/− pair returns to idle for a period of time, for example 1.0 μsec, the state a machine 304 returns to the IDLE_STATE.

At any time the PIM+/− pair is idle ($V_{PIM+}$=$V_{PIM-}$=$V_{dd}$), the echo amplifier 212 may be used to drive an echo signal from the scanner 110 to the PIM 104 via the PIM+/− pair. An exemplary echo signal is illustrated beginning at time T3.

Figure 5:
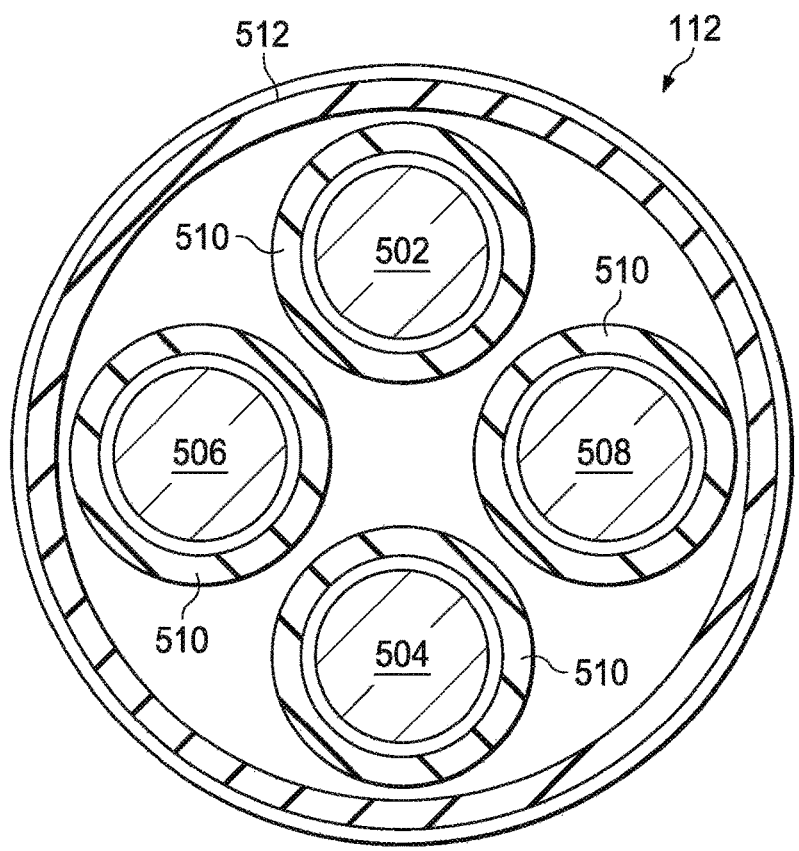
FIG. 5 is a cross-sectional view of a cable according to an embodiment of the present disclosure.

FIG. 5 is a cross-sectional view of a cable 112 according to an embodiment of the present disclosure. The cable includes four conductors 502, 504, 506, and 508. Conductors 502 and 504 are designated for transmitting a first operating voltage (High Voltage) and a ground (GND) respectively between the PIM 104 and the scanner 110. In an embodiment, the conductors 502 and 504 also provide distributed capacitance that suppresses transient voltage spikes between the common mode voltage of the 502 and 504 signal pair and/or between the common mode voltage of the 506 and 508 signal pair. As an example, a 3 m cable may have a typical capacitance of 40 to 160 pF/m.

Conductors 506 and 508 are designated PIM+ and PIM− respectively. PIM+ and PIM− are bidirectional multipurpose signals. As disclosed with reference to FIGS. 3 and 4, the PIM+/− pair configures the scanner 110 and initiates ultrasound emission and reception as well transmitting received echo data from the scanner 110 to the PIM 104. In the depicted embodiment, conductors 502, 504, 506, and 508 are arranged in a star quad configuration. By pairing conductors of opposite polarity (e.g. conductor pair 502 and 504 and conductor pair 506 and 508) the star quad configuration reduces external interference, crosstalk, and signal distortion. Compared to interface designs requiring more conductors, the cable 112 has a smaller diameter than such designs. In fact, a twisted quad such as a star quad occupies only a slightly larger cylindrical space (20% larger diameter) than a twisted pair of the same size conductors.

Reducing the number of conductors to four also decreases the stiffness of the cable. Thus, in an embodiment, a device containing a four-conductor cable is more flexible than a similar device containing a seven-conductor bundle. Additionally, in a further embodiment, the four-conductor cable allows the use of a narrower gauge device body. For example, the four-conductor cable may enable catheters 3Fr and smaller in diameter. Such sizes are preferred for interventionary cardiology applications since many balloon and stent catheters fall within this range. Devices below 3.5Fr are preferred for radial access procedures as such procedures typically use a smaller gauge guiding catheter compared to traditional femoral access.

In an embodiment, the four-conductor cable 112 requires a smaller contact area at the scanner 110 than a cable having more conductors. During assembly of the device 102, the contact area may not conform to the shape of the scanner 110 during the rolling process. This can result in a bulge at the contact area. A bulge can increase the outer diameter of the device 102, which can prevent the passage of the device 102 through constricted areas. An inward-protruding bulge has the potential to impinge on the guide wire and prevent the smooth advance of the device to a desired location. In an embodiment, the smaller contact area used in conjunction with the few-conductor cable 112 significantly reduces or eliminates the formation of such a bulge.

In an embodiment, the cable 112 incorporates thicker conductors than typical 7-conductor transmission line arrangements. A four-wire bundle of comparable diameter to a seven-wire bundle can have individual conductors with nearly twice the cross-sectional area and half the resistance. For example, a typical 7-conductor bundle may utilize 44 AWG gauge wires. 44 AWG wires are flexible but are fragile, difficult to manipulate, and possess high resistivity. In contrast, a comparable 4-conductor cable 112 may utilize 41 AWG gauge wires. Increased wire gage improves durability and reduces resistivity, which can improve signal quality.

To further improve signal transmission and reduce interference, including outside electromagnetic interference (EMI) as well as noise and crosstalk between conductors, the conductors 502, 504, 506, and 508 may be individually isolated by grounding shields 510. The grounding shields 510 reduce induced voltages in the conductors and reduce line loss. In some embodiments, the cable 112 includes an outer grounding shield 512. These electrical isolation measures, either alone or in combination with larger gauge conductors, allow the cable 112 to carry signals with greater amplitude and fidelity and with reduced distortion and interference.

Figure 6:
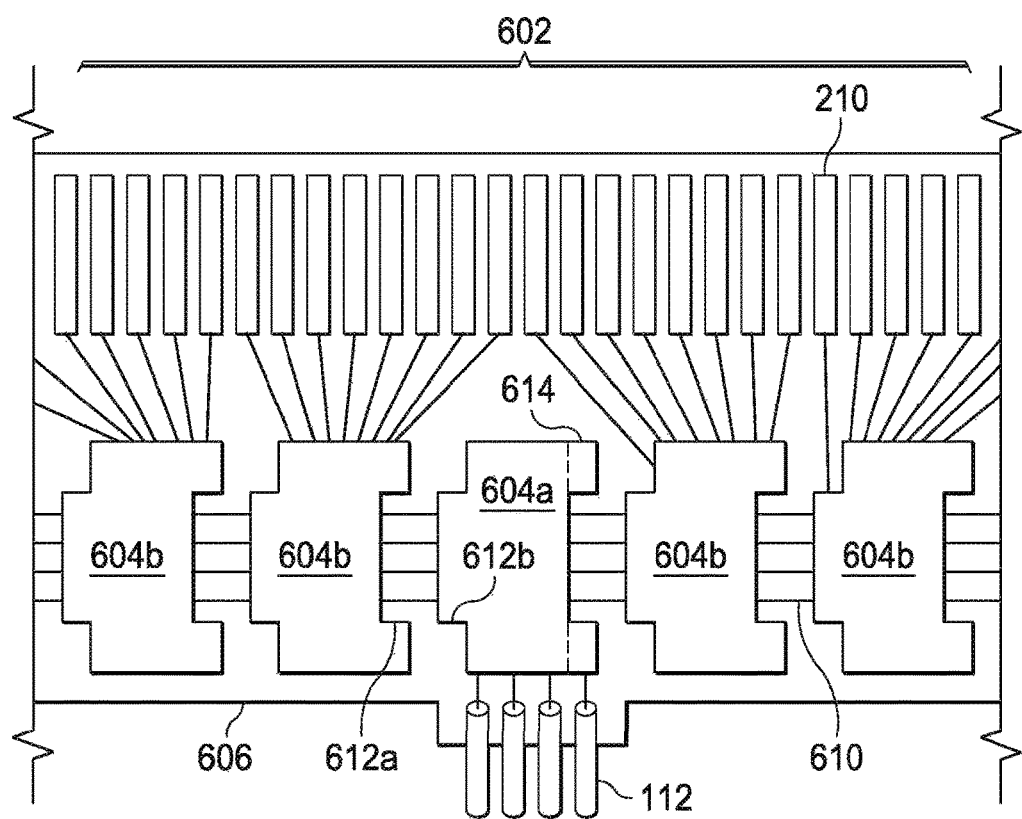
FIG. 6 is a top view of a portion of an ultrasound scanner assembly depicted in its flat form according to an embodiment of the present disclosure.

FIG. 6 is a top view of a portion of an ultrasound scanner assembly 110 according to an embodiment of the present disclosure. FIG. 6 depicts the ultrasound scanner assembly 110 in its flat form. The assembly 110 includes a transducer array 602 and transducer control circuits 604 (including controllers 604a and 604b) attached to a flex circuit 606. As indicated by the common reference numbers, the ultrasound transducers 210 of the transducer array 602 are substantially similar to those disclosed with reference to FIG. 2. The transducer array 602 may include any number and type of ultrasound transducers 210, although for clarity only a limited number of ultrasound transducers are illustrated in FIG. 6. In an embodiment, the transducer array 602 includes 64 individual ultrasound transducers 210. In a further embodiment, the transducer array 602 includes 32 ultrasound transducers. Other numbers are both contemplated and provided for. In an embodiment, the ultrasound transducers 210 of the transducer array 602 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

In the illustrated embodiment, scanner 110 having 64 ultrasound transducers 210 includes nine transducer control circuits 604, of which five are shown. Designs incorporating other numbers of transducer control circuits 604 including 8, 9, 16, 17 and more are utilized in other embodiments. In some embodiments, a single controller is designated a master controller and configured to receive signals directly from the cable 112. The remaining controllers are slave controllers. In the depicted embodiment, the master controller 604a does not directly control any transducers 210. In other embodiments, the master controller 604a drives the same number of transducers 210 as the slave controllers 604b or drives a reduced set of transducers 210 as compared to the slave controllers 604b. In the illustrated embodiment, a single master controller 604a and eight slave controllers 604b are provided. Eight transducers are assigned to each slave controller 604b. Such controllers may be referred to as 8-channel controllers based on the number of transducers they are capable of driving.

The master controller 604a generates control signals for the slave controllers 604b based on configuration data and transmit triggers received via the cable 112. The master controller 604a also receives echo data from slave controllers 604b and retransmits it on the cable 112. To do so, in some embodiments, the master controller 604a includes the echo amplifier 212 of FIG. 2. In this configuration, the master controller 604a receives unamplified or partially amplified echo data and performs the necessary amplification for driving the echo data along the conductors 506 and 508 of the cable 112. This may provide additional room for a larger high-fidelity amplifier.

In an embodiment, the flex circuit 606 provides structural support and physically connects the transducer control circuits 604 and the transducers 210. The flex circuit 606 may contain a film layer of a flexible polyimide material such as KAPTON™ (trademark of DuPont). Other suitable materials include polyester films, polyimide films, polyethylene napthalate films, or polyetherimide films, other flexible printed circuit substrates as well as products such as Upilex® (registered trademark of Ube Industries) and TEFLON® (registered trademark of E.I. du Pont). The film layer configured to be wrapped around a ferrule to form a cylindrical toroid in some instances. Therefore, the thickness of the film layer is generally related to the degree of curvature in the final assembled scanner 110. In some embodiments, the film layer is between 5 µm and 100 µm, with some particular embodiments being between 12.7 µm and 25.1 µm.

In an embodiment, the flex circuit 606 further includes conductive traces 610 formed on the film layer. Conductive traces 610 carry signals between the transducer control citron 604 and the transducers 210 and provide a set of pads for connecting the conductors of cable 112. Suitable materials for the conductive traces 610 include copper, gold, aluminum, silver, tantalum, nickel, and tin and may be deposited on the flex circuit 606 by processes such as sputtering, plating, and etching. In an embodiment, the flex circuit 606 includes adhesion layer. The width and thickness of the conductive traces are selected to provide proper conductivity and resilience when the flex circuit 606 is rolled. In that regard, an exemplary range for the thickness of a conductive trace 610 is between 10-50 µm. For example, in an embodiment, 20 µm conductive traces 610 are separated by 20 µm space. The width of a conductive trace 610 may be further determined by the size of a pad of a device or the width of a wire to be coupled to the trace.

As the circuit may be rolled to form the finished scanner assembly, the control circuits 604, including both master and slave controllers, may be shaped accordingly. This may include a control circuit 604 edge configured to interface with an edge of an adjacent control circuit 604. In some embodiments, the control circuits 604 include interlocking teeth 612a and 612b. For example, control circuits 604 may be formed with a recess and projection 612a that interlocks with a recess and projection 612b of an adjacent control circuit 604 to form a box joint or finger joint. In some embodiments, a control circuit 604 includes a chamfered edge 614, either alone or in combination with a recess and projection. The chamfered edge 614 may be configured to abut an edge of an adjacent control circuit 604. In some such embodiments, the edge of the adjacent controller is chamfered as well. In some embodiments, each of the controllers 604 interlocks with two adjacent controllers utilizing a similar recess and projection interface. Other combinations, including embodiments utilizing a number of different mechanisms, are contemplated and provided for. For example, in an embodiment, edges of slave control circuits interfacing with a master control circuit have a recess and projection configuration with a chamfered region while edges of slave control circuits interfacing with other slave control circuits have a recess and projection configuration without a chamfered region. Edge configurations that interlock adjacent control circuits 604 may allow for closer control circuit spacing 604 and a reduced diameter in the rolled configuration. Such configurations may also interlock to create a rigid grunge and thereby provide additional structural support for the rolled scanner assembly.

Figure 7:
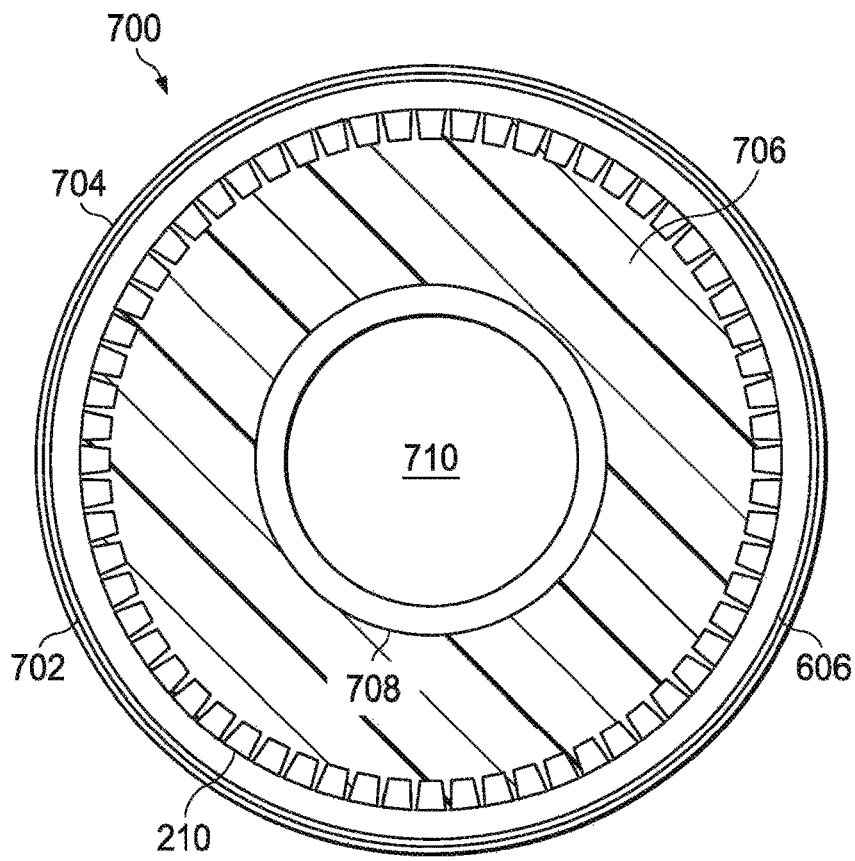
FIG. 7 is a cross-sectional view of a transducer region of are ultrasound scanner assembly according to an embodiment of the present disclosure.

FIG. 7 is a cross-sectional view of a transducer region 700 of an ultrasound scanner assembly 110 according to an embodiment of the present disclosure. The transducer region 700 is depicted in its rolled form. In that regard, in some instances the scanner is transitioned from a flat configuration to a rolled or more cylindrical configuration. For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,418, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

As the name implies, the transducer region 700 of the scanner contains the transducers 210, which, as previously disclosed, are attached to the flex circuit 606, and in particular, to the traces of the flex circuit 606. In the illustrated embodiment, the flex circuit 606 also includes a conductive ground layer 702. In a further embodiment, the flex circuit includes an outer membrane 704 used to insulate and cover the ground layer 702 and to protect the scanner 110 from the environment. Insulator materials for the outer membrane 704 may be selected for their biocompatibility, durability, hydrophilic or hydrophobic properties, low-friction properties, ultrasonic permeability, and/or other suitable criteria. For example, the outer membrane may include Parylene™ (trademark of Union Carbide). Other suitable materials include heat shrink tubing such as polyester or PVDF, a melt-formable layers such as Pebax® (registered trademark of Arkema) or polyethylene, and/or other suitable membrane materials. In some instances, encapsulating epoxy 706 fills the spaces between the ultrasound transducers 210 and the ferrule 708. The lumen region 710 inside the ferrule 708 is open to allow the scanner 110 to be advanced over a guide wire (not shown). As can be seen, the size, shape, and spacing of the ultrasound transducers 210 at least partially define the shape of the transducer region 700. In embodiments with 64 ultrasound transducers 210, the cross-section the transducer region is circular or nearly circular.

Figure 8A:
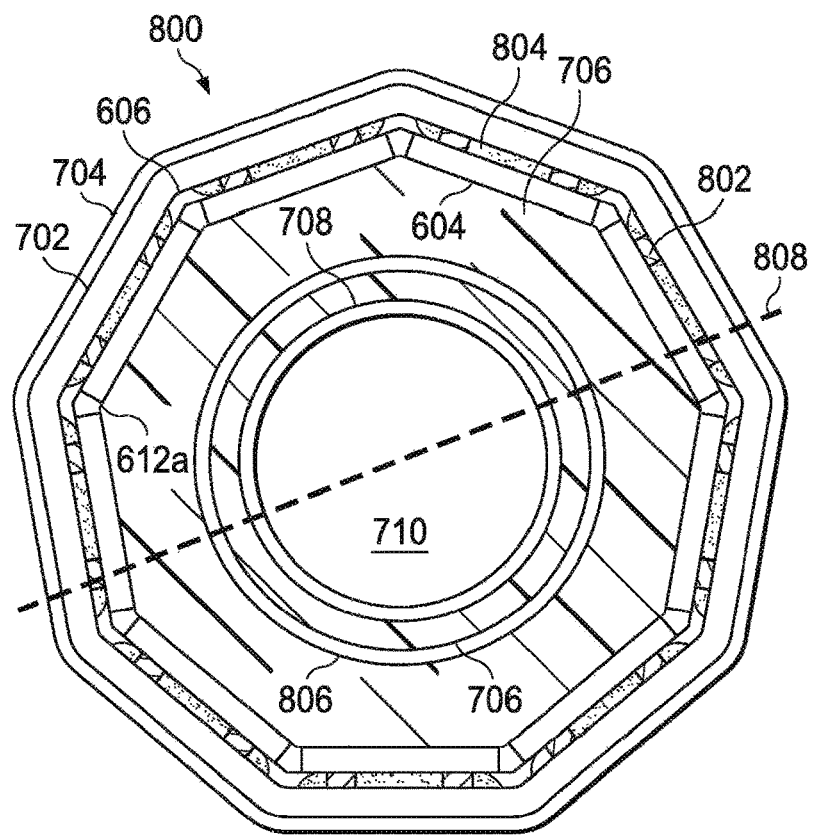
FIGS. 8a and 8b are cross-sectional views of control regions ultrasound scanner assemblies according to embodiments of the present disclosure.
Figure 8B:
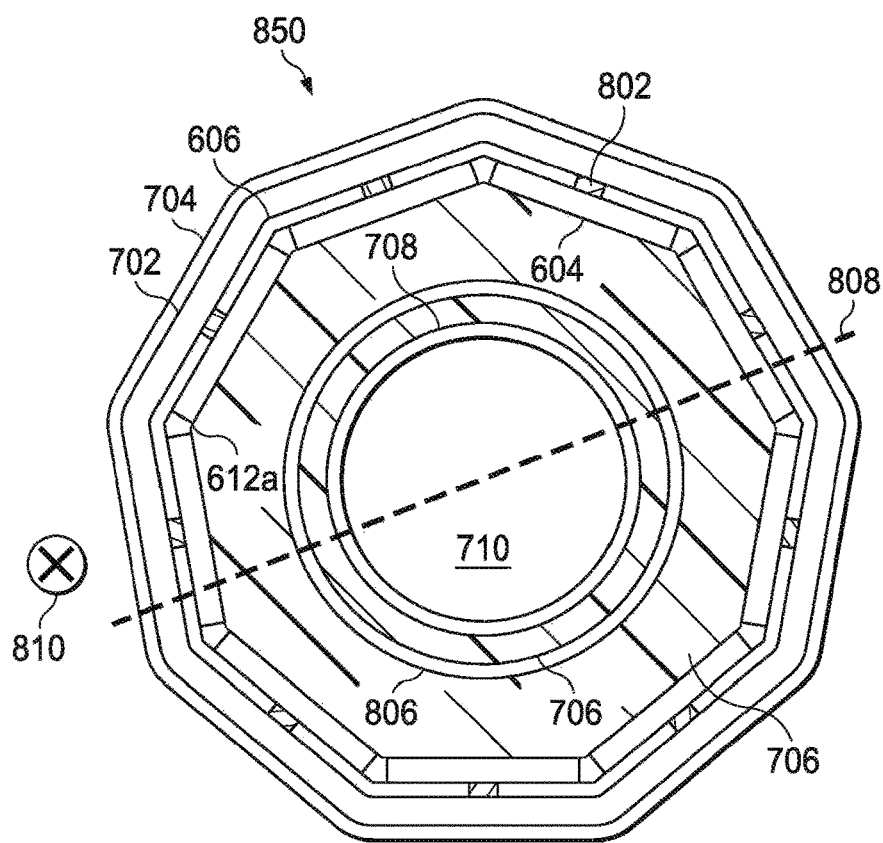

FIGS. 8a and 8b are cross-sectional views of control regions 800 and 850 of an ultrasound scanner assembly 110 according to embodiments of the present disclosure. Referring first to FIG. 8a, the control region 800 contains the transducer control circuits 604 bonded to the flex circuit 606. In some embodiments, the control circuits 604 include contact bumps 802 coupling the control circuit to the traces of the flex circuit 606. The contact bumps 802 may include a metal core, such as a copper core, with a solder portion. During formation, the contact may be heated, causing the solder to flow and join the metal core of the contact bump 802 to the flex circuit 606 trace. An underfill material 804 between the control circuits 604 and the flex circuit 606, may be applied to increase the bond strength, to provide structural support for the control region 800, to insulate conductive structures including the contact bumps 802, and/or to promote thermal conduction.

In an embodiment, the control region 800 includes a retaining structure 806 applied over the transducer control circuits 604. The retaining structure 806 may be used during the rolling process, for example, to secure components including the control circuits 604, Encapsulating epoxy 706 fills the space between the transducer control circuits 604 and the retaining structure 806 and between the retaining structure 806 and the ferrule 708 in some embodiments. Similar to the transducer region 700, the transducer control circuits 604 at least partially define the shape of the transducer region. Because portions, of the flex circuit 606 adjacent to the transducer control circuits 604 are flat, utilizing narrower and more numerous transducer control circuits 604 in place of larger controllers produces a more circular cross-section. It follows that designs utilizing 8, 9, 16, or more transducer control circuits 604 will have a more circular cross-section than designs with 4 or 5 controllers. This has the advantage of reducing the effective diameter 808 of the scanner 110 and of reducing the length of the transition zone along the longitudinal axis of the device 102 as will be discussed below.

As illustrated, the control circuits 604 may be configured to contact adjacent control circuits in the rolled configuration. This may include interlocking recesses and/or projections (e.g., recess and projection 612a), chamfered edges, and/or other edge profiles. In the illustrated embodiment, each of the controllers 604 interlocks with two adjacent controllers utilizing a recess and projection interface. Other combinations, including embodiments utilizing a number of different mechanisms, are contemplated and provided for. For example, in an embodiment, edges of slave control circuits interfacing with a master control circuit have a recess and projection configuration with a chamfered region while edges of slave control circuits interfacing with other slave control circuits have a recess and projection configuration without a chamfered region.

With respect to FIG. 8b, the control region 850 is substantially similar to control region 800 of FIG. 8a. In the illustrated embodiment, the contact bumps 802 of the control circuits 604 are configured to allow the encapsulating epoxy 706 to fill the void between the control circuits 604 and the flex circuit 606. This may eliminate the need for an underfill material saving manufacturing time and expense. It may also eliminate a material junction between the underfill material and the encapsulating epoxy 706 and thereby avoid a potential point of failure. In order to allow the encapsulating epoxy 706 to flow between the control circuits 604 and the flex circuit 606, the contact bumps 802 may have a different aspect ratio than those of an underfill application, for example being longer in a longitudinal direction. In some embodiments, such as that illustrated in FIG. 8b, the contact bumps 802 are aligned along a single axis (e.g., axis 810, perpendicular to the plane of the illustrated cross section). This may improve the flow of the encapsulating epoxy 706 between the control circuits 604 and the flex circuit 606.

Figure 9:
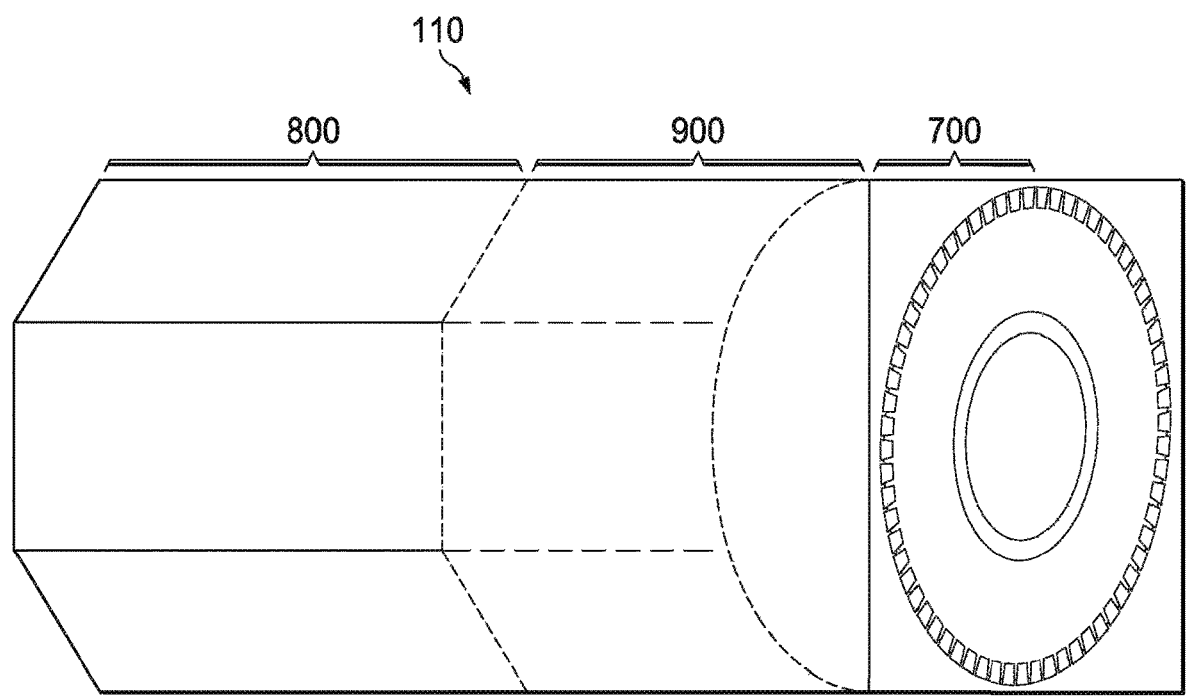
FIG. 9 is a longitudinal perspective view of a portion of an ultrasound scanner assembly depicted in its rolled form according to an embodiment of the present disclosure.

FIG. 9 is a longitudinal perspective view of a portion of an ultrasound scanner assembly depicted in its rolled form according to an embodiment of the present disclosure. Referring to FIG. 9, the transition zone 900 is located between the transducer region 700 and the control region 800. In contrast to the transducer region 700 and the control region 800, the transition zone 900 is free of rigid structures. Instead, the cross-sectional shape is defined by the adjacent regions 700 and 800. Thus, the shape of the transition zone 900 transitions between that of the transducer region 700 and the controller region 800. The transition zone 900 may be used to reduce sharp angles that can stress the flex circuit 606 and/or the conductive traces 610. Because of the more circular cross-section of the associated controller region 800 of the present disclosure, embodiments utilizing, for example, 8, 9, 16, or more transducer control circuits 604 support a shorter transition zone 900. In other words, because both transducer control circuits 604 and ultrasound transducers 210 produce flat areas within the flex circuit 606, substituting physically narrower devices reduces the non-circular regions of the flex circuit 606 caused by each individual device. Therefore, a design utilizing, for example, nine transducer control circuits has a more cylindrical controller region 800 than a design utilizing four transducer control its and likewise accommodates a shorter transition zone 900. In an exemplary four-control circuit embodiment, the transition zone 900 is approximately 1 to 1.5 catheter diameters in order to transition from square to substantially round. This works out to be between 1000 and 1500 µm for a 3Fr catheter. In an exemplary nine-control circuit embodiment, the transition zone 900 is approximately 0.5 to 0.75 catheter diameters, or between 500 and 750 µm for a 3Fr catheter.

As previously explained, eight channel controllers are capable of operating up to eight transducers, whereas sixteen channel controllers are capable of operating up to sixteen transducers. In an embodiment with 64 transducers, the eight channel controller used in an nine controller design (with one master controller and eight slave controllers) is physically shorter than a sixteen channel controller such as that used in a comparable five controller implementation. A four channel controller may be shorter than even the eight channel controller. In this way, designs incorporating fewer channels per controller may produce a shorter scanner assembly 110. Because the scanner assembly 110 is typically inflexible or rigid compared to the surrounding portion of the device, reducing the length of the assembly 110 results in a more agile IVUS catheter capable of maneuvering through complex vascular branches and producing less discomfort in the patient.

Figure 10:
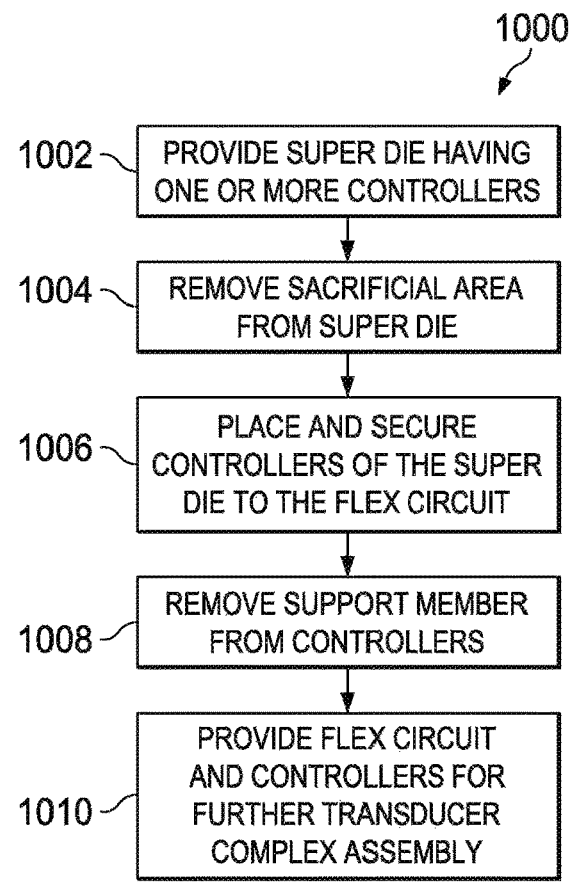
FIG. 10 is a flow diagram of a method of manufacturing an ultrasound scanner assembly utilizing a super-die according to an embodiment of the present disclosure.
Figure 11:
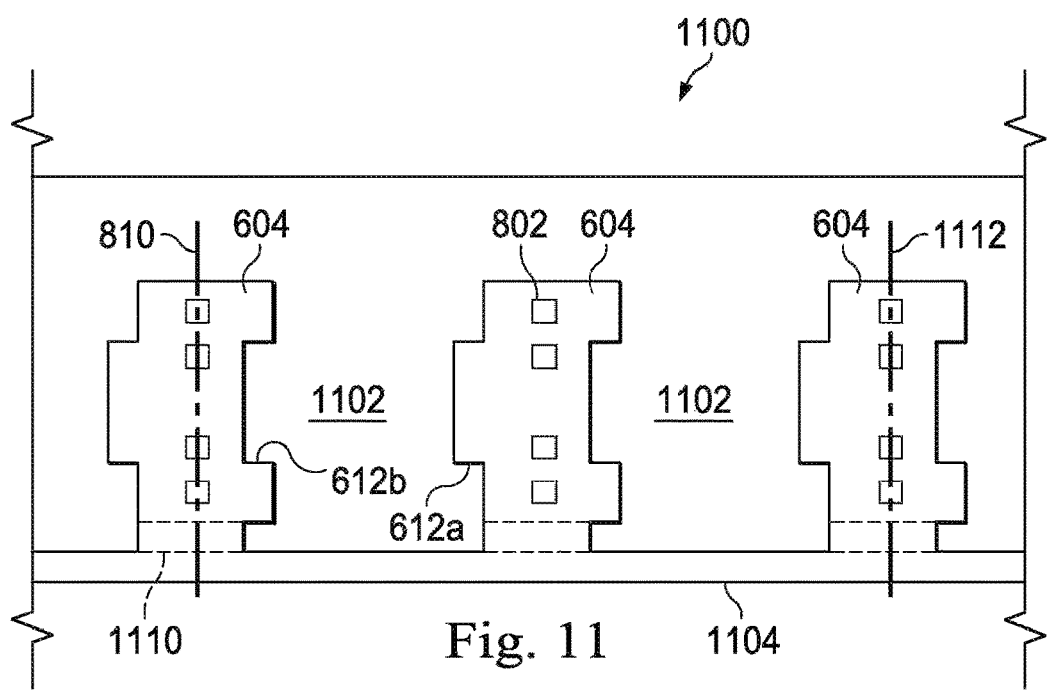
FIG. 11 is a simplified top view of a super-die for use in an IVUS imaging device according to an embodiment of the present disclosure.

A method 1000 of manufacturing an ultrasound scanner assembly utilizing a super-die 1100 is described with reference made to FIGS. 10-13. FIG. 10 is a flow diagram of the method 1000 of manufacturing the ultrasound scanner assembly 110 utilizing a super-die 1100 according to an embodiment of the present disclosure. It is understood that additional steps can be provided before, during, and after the steps of method 1000, and some of the steps described can be replaced or eliminated for other embodiments of the method, FIG. 11 is a simplified top view of a super-die 1100 for use in an IVUS imaging device according to an embodiment of the present disclosure. FIG. 12 is a simplified cross-sectional view of a super-die 1100 taken along an axis indicated in FIG. 11 according to an embodiment of the present design. FIG. 13 is a top vie r of a portion of an ultrasound scanner assembly 110 in a stage of manufacturing according to an embodiment of the present disclosure. The super-die 1100 contains a plurality of transducer control circuits 604 intended for use in a single scanner 110. For clarity, FIGS. 11 and 13 show a limited number of controllers 604. However, it is understood that the present disclosure contemplates super-dies incorporating any number of controllers. In various embodiments, the number of controllers ranges from as few as four to as many as one per transducer element. Furthermore, to be able to clearly illustrate elements of the present disclosure, FIGS. 11-13 are not necessarily drawn to scale. In fact, the dimensions of the various features may be arbitrarily increased or reduced for clarity of discussion.

Referring to FIG. 11, in an exemplary embodiment, the small size of each individual transducer control circuit 604 causes problems during fabrication and assembly. For example, in a 16-controller, 64-transducer design, each die may be on the order of 100 µm wide. This small footprint can lead to device loss during dicing and can make the controllers 604 difficult to handle and manipulate. This proves especially problematic when securing the controllers 604 to the flex circuit 606. Referring to block 1002 of FIG. 10 and referring still to FIG. 11, in an embodiment, a super-die 1100 having one or more controllers 604 is provided. The super-die 1100 is designed to act as a framework for the controllers 604 during assembly of the scanner. As such, the controllers 604 are spaced apart by a sacrificial area 1102. In some embodiments, the amount of sacrificial area 1102 between controllers 604 is determined by the final positioning of the controllers on the flex circuit. In one such embodiment, the pitch width of the controllers 604 (i.e., the spacing between adjacent controllers) on the super-die 1100 is the same as the pitch width of the mounting locations of the controllers 604 on the flex circuit. To further aid in assembly, in an embodiment, the sacrificial area 1102 includes a scribe line, a region used when dicing the controllers 604 to remove a portion of the sacrificial area 1102.

The sacrificial area 1102 may also include a support member 1104 adjacent to the controllers 604. The support member 1104 maintains the alignment of the controllers 604 during processing and may be formed as part of the same substrate that forms the controllers 604 and the sacrificial area 1102. The support member 1104 may also be a separate material, for example a rigid material, releasably adhered to the set of controllers 604. In an embodiment, the super die 1100 contains one support member 1104 attached to all of the controllers 604. In an alternate embodiment, the super-die contains more than one support member 1104, each attached to two or more controllers 604 such that every controller is attached to at least one other controller. In some embodiments, the support member 1104 includes a cleavage junction 1110 to facilitate removal of the support member 1104. An exemplary cleavage junction 1110 includes a recessed or thinned region configured to create a fracture point.

As the controllers may b incorporated into a rolled scanner assembly, the control it its 604, including both master and slave controllers, may be shaped to provide additional support in the rolled form. To do so, control circuits 604 may include an edge configured to interface with an edge of adjacent control circuits 604. In some embodiments, the control circuits 604 include interlocking teeth 612a and 612b. For example, control circuits 604 may formed with a recess and projection 612a that interlocks with a recess and projection 612b of an adjacent control circuit 604 to form a box joint or finger joint. In such embodiments, the shape of the sacrificial area 1102 is configured to accommodate the shape of the control circuits 604.

The controllers 604 may include contact bumps 802 to electrically couple the controllers 604 to a substrate as disclosed above. In the illustrated embodiment, the contact bumps 802 of the control circuits 604 are configured to allow encapsulating epoxy to fill the void between the control circuits 604 and the flex circuit 606. This may eliminate the need for an underfill material saving manufacturing time and expense and avoiding a material junction and a potential point of failure. In some embodiments, such as that illustrated in FIG. 11, the contact bumps 802 are aligned along a single axis (e.g., axis 810). This may improve the flow of the encapsulating epoxy between the control circuits 604 and the flex circuit 606.

FIG. 12 illustrates a cross section of the module 1100 taken along the axis 1112 of FIG. 11. The module 1100 includes a substrate 1200 upon which the transducer control circuits 604 are formed. Substrate 1200 may be a wafer, a semiconductor substrate, or any base material on which processing is conducted to produce layers of material, pattern features, and/or integrated circuits such as those used to manufacture a transducer control circuit 604. Examples of semiconductor substrates include a bulk silicon substrate, an elementary semiconductor substrate such as a silicon or germanium substrate, a compound semiconductor substrate such as a silicon germanium substrate, an alloy semiconductor substrate, and substrates including non-semiconductor materials such as glass and quartz. An exemplary method for forming the controllers 604 includes growing a pad oxide layer over the substrate, depositing a nitride layer by chemical vapor deposition, reactive ion etching to form a trench, growing a shallow isolation feature oxide, chemical-mechanical planarization, channel implantation, formation of a gate oxide, polysilicon deposition, etching to form a gate structure, source-drain implantation, forming of sidewall spacers, self-aligned silicide process, formation of one or more interconnect layers, formation of a pad layer, and/or other fabrication processes known to one of skill in the art. In some instances, the method for forcing the controllers 604 produces gate structures 1202, shallow trench isolation features 1204, conductive layers 1206, insulator layers 1208, and/or contact bumps 802. In an embodiment, the method includes forming a cleavage junction 1110 in the support member 1104 at a location adjacent to the controller 604. In the illustrated embodiment, forming the cleavage junction 1110 includes performing an etching of the substrate 1200 and layers formed above the substrate 1200 to define the cleavage junction 1110.

Referring again to FIG. 10, in block 1004, a portion of the sacrificial area not corresponding to the support member 1104 is removed from the super-die, in some instances, the sacrificial area 1102 is removed by a process that includes chemical etching (such as wet or dry etching), laser etching, mechanical sawing, and/or other suitable etching or removal process. In some embodiments, the removing of the sacrificial area includes forming a photoresist layer on the super-die 1100, performing a photolithographic exposure of the photoresist layer, patterning of the exposed photoresist, and/or etching of the super-die 1100 based on the patterned photoresist. In an embodiment, the removal process includes one or more deep reactive-ion etching processes utilizing fluorine-containing etchant such as sulfur hexafluoride, and one or more depositions of a passivation layer.

Referring to block 1006 of FIG. 10 and FIG. 13, the controllers 604 are then placed as a unit and secured, such as by conductive adhesive or soldering, to a flex circuit 606. In some embodiments, the flex circuit 606 includes an underfill material configured to secure the controllers 604 to the flex circuit 606. The remaining support member 1104 maintains the alignment and spacing of the controllers 604 during placement. In an embodiment, the support member 1104 provides a contact point for an automated tool such as an assembly robot. In an example of such an embodiment, the support member 1104 is grasped by the automated manufacturing tool. The tool places the controllers 604 on the flex circuit 606 utilizing the support member 1104. The controllers 604 are then secured to the flex circuit 606, Thereafter, the automatic manufacturing tool release the support member 1104.

In block 1008 of FIG. 10, in an embodiment, the support member 1104 is removed from the controllers 604 once the controllers 604 are fixed to the flex circuit 606. Suitable methods for separating the support member 1104 include physical force, saw dicing, mechanical cutting, laser cutting, and other suitable removal processes. In embodiments having a support member 1104 with a cleavage junction 1110, separating the support member may involve directing force along the cleavage junction 1110 to facilitate removal. In block 1010 of FIG. 10, the flex circuit 606 is provided to a finishing facility for final assembly, which may include applying a retaining structure 806, rolling or otherwise shaping the flex circuit 606, applying an encapsulating epoxy 706, attaching the cable 112, and/or sealing the scanner 110.

Utilizing a support member in combination with a sacrificial area designed to ensure proper spacing and alignment of the controllers 604 greatly improves manufacturability of the scanner. For example, in some embodiments, the super-die 1100 allows for faster and more accurate assembly of the scanner. This improves efficiency and reduces misalignment errors and lost yield. In some embodiments, the super-die 1100 allows the use of automated pick-and-place equipment to assemble the scanner. As discussed above, the support member 1104 provides a contact point for the pick-and-place equipment in some instances. The improved manufacturing precision also allows the super-die 1100 to be assembled from smaller components. This can reduce the overall outer diameter of the scanner 110 and of the IVUS catheter 102.

Figure 14:
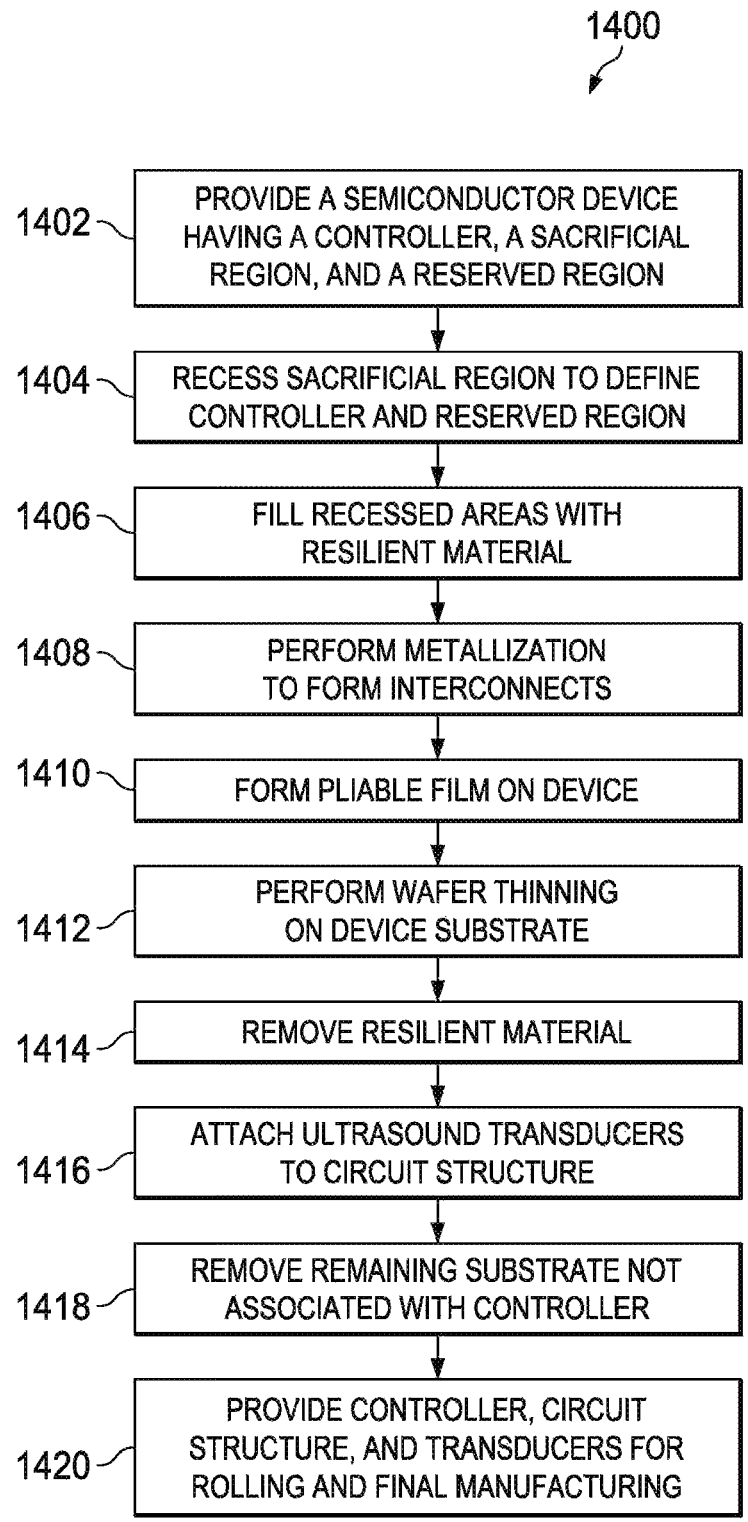
FIG. 14 is a flow diagram of a method of wafer-based microassembly of an ultrasound scanner assembly according to an embodiment of the present disclosure.
Figure 23:
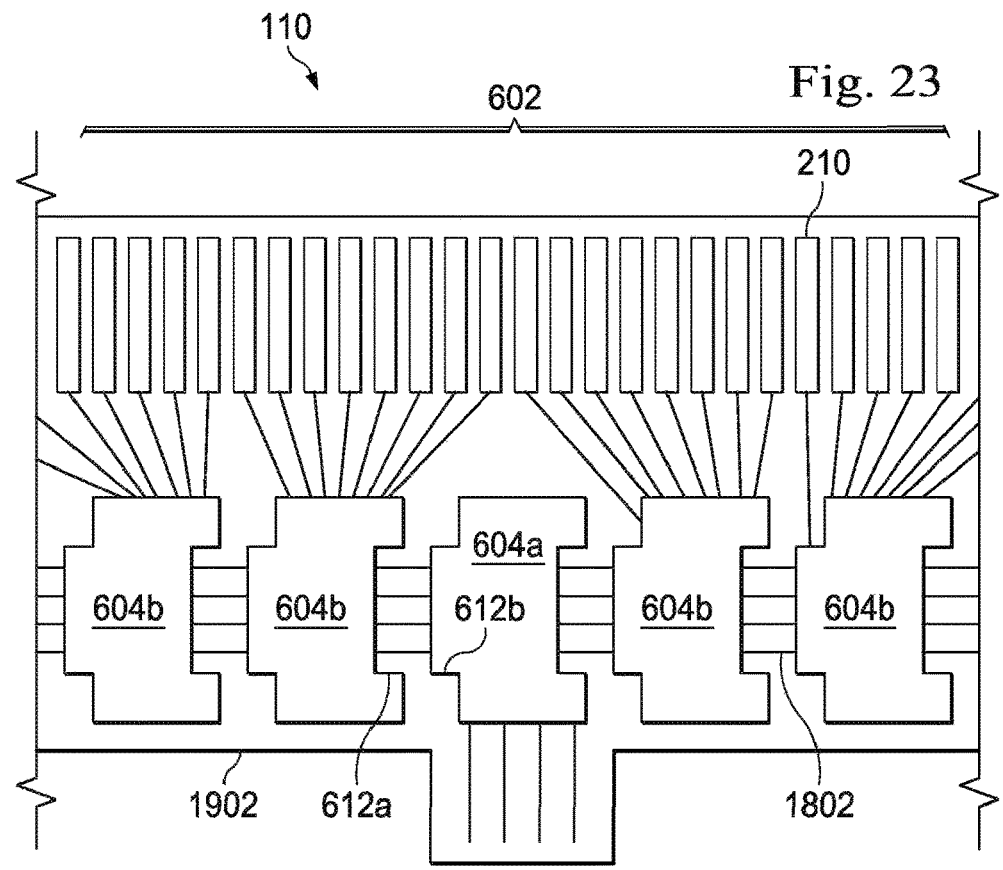
FIG. 23 is a top view of a portion of a semiconductor device in a stage of microassembly according to an embodiment of the present disclosure.

Referring now to FIGS. 14-22, a method 1400 of wafer-based microassembly of an ultrasound scanner assembly 110 is described. FIG. 14 is a flow diagram of the method 1400 of wafer-based microassembly of an ultrasound scanner assembly according to an embodiment of the present disclosure. It is understood that additional steps can be provided before, during, and after the steps of method 1400, and some of the steps described can be replaced or eliminated for other embodiments of the method, FIG. 15 is a top view of a portion of a semiconductor device in a stage of microassembly according to an embodiment of the present disclosure. FIGS. 16-22 are simplified cross-sectional views of a semiconductor device 1500 in various stages of the method 1400 of microassembly according to an embodiment of the present disclosure. To be able to clearly illustrate elements of the present disclosure, FIGS. 15-22 are not necessarily drawn to scale. In fact, the dimensions of the various features may be arbitrarily increased or reduced for clarity of discussion. FIG. 23 is a top view of a portion of an ultrasound scanner assembly in a stage of microassembly according to an embodiment of the present disclosure. For clarity, FIGS. 15 and 23 show only five controllers 604. However, it is understood that the present disclosure contemplates super-dies incorporating any number of controllers including 4, 5, 8, 9, 16, and more controllers per module.

Referring to block 1402 of FIG. 14 and FIG. 15, a semiconductor device 1501 is provided that includes a transducer control circuit 604 along with a sacrificial region 1502 and a reserved region 1504 corresponding to an area reserved for one or more transducers 210. The semiconductor device 1500 includes a substrate 1501, which may be a wafer, a semiconductor substrate, or any base material on which processing is conducted to produce layers of material, pattern features, and/or integrated circuits such as those used to manufacture a transducer control circuits including transducer control circuits 604a and 604b. The fabrication of a controller 604 on the substrate 1501 may be substantially similar to that described with reference to FIG. 12.

As the controllers may be incorporated into a rolled scanner assembly, the control circuits 604, including both master and slave controllers, may be shaped to provide additional support in the rolled form. To do so, control circuits 604 may include an edge configured to interface with an edge of adjacent control circuits 604. In some embodiments, the control circuits 604 include interlocking teeth 612a and 612b. For example, control circuits 604 may be formed with a recess and projection 612a that interlocks with a recess and projection 612b of an adjacent control circuit 604 to form a box joint or finger joint. In such embodiments, the shape of the sacrificial region 1502 is configured to accommodate the shape of the control circuits 604.

Referring to block 1404 of FIG. 14 and FIG. 16, the substrate 1501 within the sacrificial region 1502 is recessed to form a first recess 1604 that defines an outer boundary the controller 604 and to form a second recess 1606 within the reserved region 1504 that defines an eventual location for a transducer 210. In an embodiment, the first and second recesses 1604 and 1606 are joined. In a further embodiment, a portion of the sacrificial region 1502 is left unetched to form an alignment structure 1602. Utilizing an alignment structure 1602 allows for rapid and accurate placement of the transducers 210 later in the manufacturing process. The sacrificial region 1502 may be recessed by a process that includes chemical etching (such as wet or dry etching), laser etching, mechanical sawing, and/or other suitable etching or removal process. In some embodiments, the removing of the sacrificial area includes forming a photoresist layer on the substrate 1501, photolithographic exposure of the photoresist layer, patterning of the exposed photoresist, and/or etching of the substrate 1501 based on the patterned photoresist. In an embodiment, the removal process includes one or more deep reactive-ion etching processes utilizing fluorine-containing etchant such as sulfur hexafluoride, and one or more depositions of a passivation layer.

Referring to block 1406 of FIG. 14 and FIG. 17, the first and second recesses 1604 and 1606 are filled with a resilient material 1702. Exemplary resilient materials for filling the etched area include polydimethysiloxane (PDMS). In an embodiment, after performing the fill, a circuit structure is formed on the substrate. For example, referring to block 1408 of FIG. 14 and FIG. 18, a metallization process is performed to form interconnect layer 1802. In some embodiments, metallization includes forming a layer of conductive material, such as copper, gold, aluminum, silver, tantalum, and/or tin, and thereafter patterning the conductive layer utilizing a patterning method. Examples of such patterning methods include photolithography (such as binary photolithography, phase shift photolithography, and maskless photolithography) coupled with etching (such as wet or dry etching), as well as methods such electron beam writing, ion beam writing, and/or other alternative patterning techniques. In alternate embodiments, the metallization process includes depositing a resist layer such as a polyimide or a semiconductor nitride resist layer, patterning the resist layer, applying conductive material to the patterned resist layer, and thereafter planarizing the applied conductive material. Metallization processes of this type may be recognized by those of skill in the art as damascene metallization.

Figure 19:
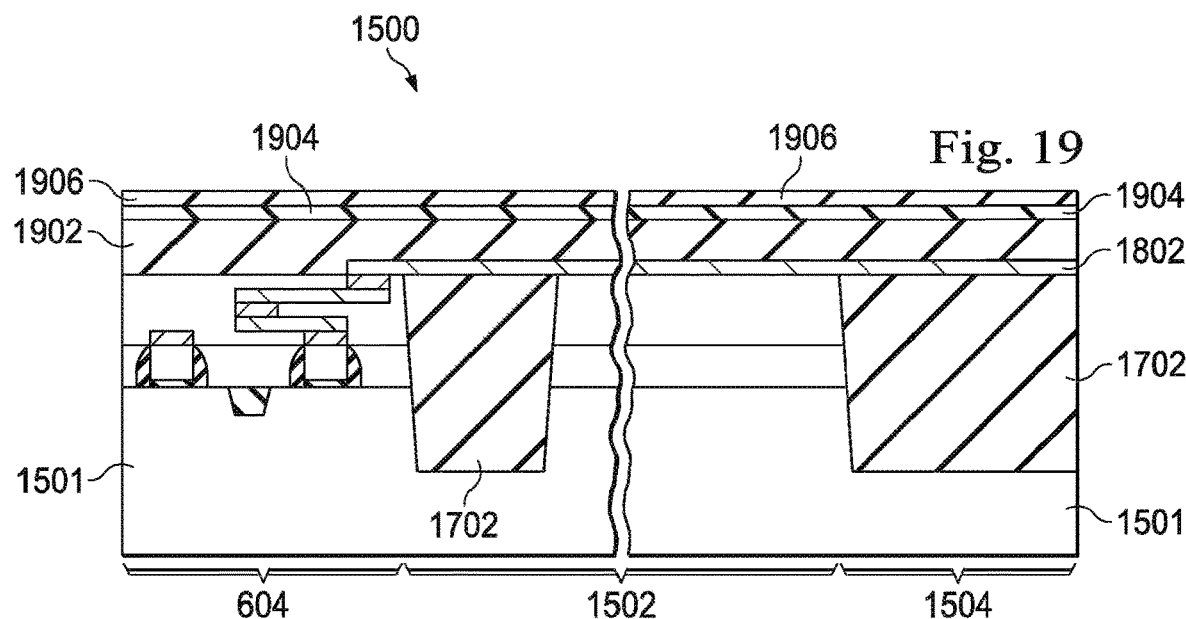

Referring to block 1410 of FIG. 14 and FIG. 19, a pliable film 1902 is formed over the interconnect layer 1802. In various embodiments, the pliable film 1902 includes a flexible polyimide material such as KAPTON™ (trademark of DuPont), other polyimide film material, polyester film material, polyethylene napthalate film material, polyetherimide film material, and/or other flexible printed circuit substrates. In an embodiment, a conductive material is formed over the pliable substrate to form a ground layer 1904. An outer insulating layer 1906 is formed over the ground layer 1904, in some embodiments. Materials for the outer insulating layer 1906 may be selected for their biocompatibility, durability, hydrophilic or hydrophobic properties, low-friction properties, ultrasonic permeability, and/or other suitable criteria. In some instances, the interconnect layer 1802, the pliable film 1902, the ground layer 1904, and the outer insulating layer 1906 perform substantially the same function as the flex circuit 606 described with reference to FIG. 6.

Figure 20A:
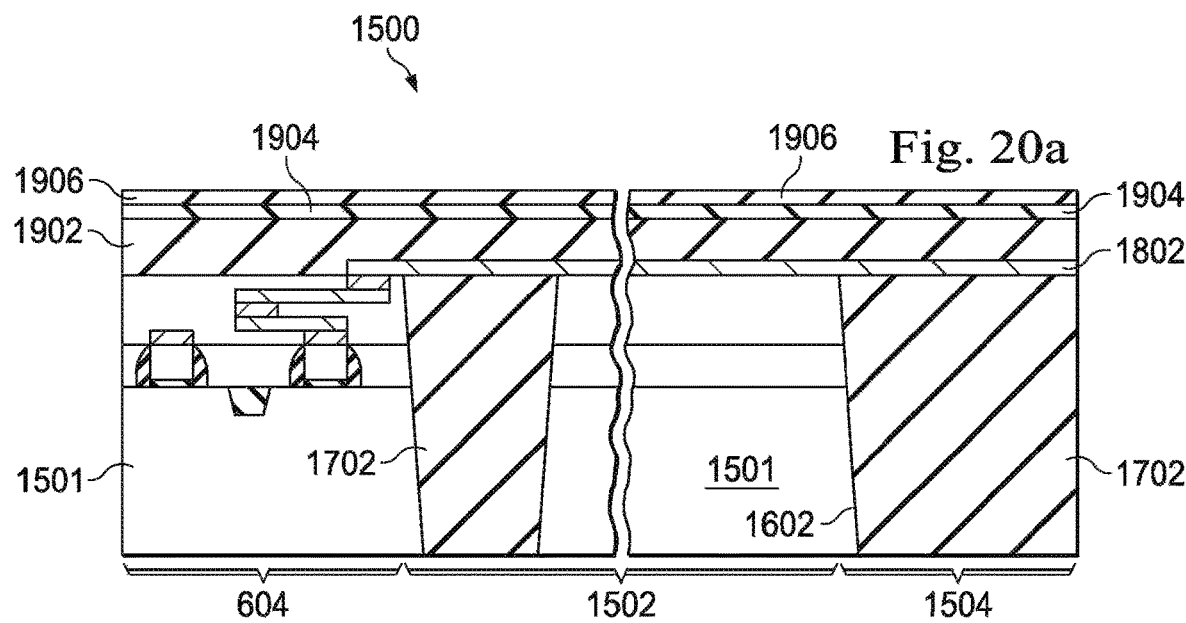
FIG. 20a is a cross-sectional side view of a semiconductor device similar to that of FIG. 19 showing a substrate having undergone a wafer thinning process.
Figure 22:
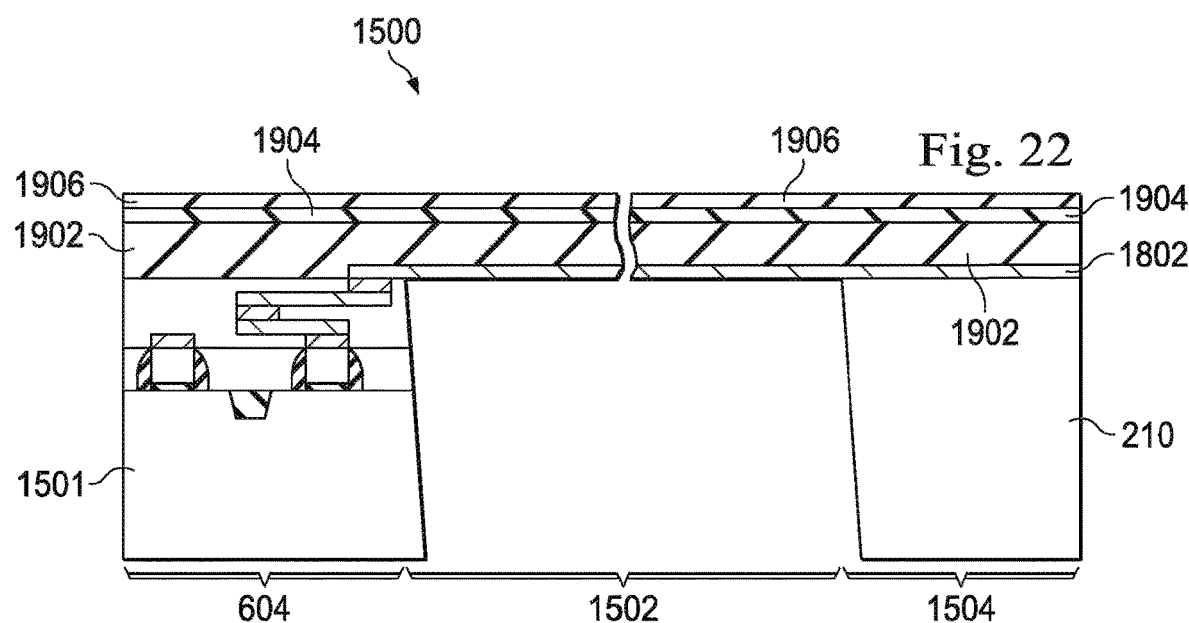

Referring to block 1412 of FIG. 14 and FIG. 20a, a wafer thinning process removes a portion of the semiconductor substrate 1501 from the bottom or backside of the substrate 1501 as viewed in FIGS. 19 and 20. Thinning may include mechanical grinding, wet or dry etching, chemical-mechanical polishing, and/or other removal processes. In an embodiment, the wafer thinning process mechanical grinding of the substrate 1501. Mechanical grinding uses abrasive force to remove substrate material. In another embodiment, the wafer thinning process includes chemical-mechanical polishing (CMP). In an exemplary CMP process, a polishing pad is installed on a rotating platen. A slurry of reactive compounds such as $NH_4OH$ and/or abrasive particles such as silica ($SiO_2$), alumina ($Al_2O_3$), and ceria ($CeO_2$) is dispensed on the polishing pad. The substrate 1501, secured in a CMP chuck, is forced against the polishing pad as both the platen and the CMP chuck rotate. The reactants the slurry loosen atomic bonds within the surface of the substrate 1501, while the mechanical abrasion removes the loosened material. CMP is typically slower than purely mechanical grinding but produces less damage to the substrate 1501.

Referring to block 1414 of FIG. 14 and FIG. 20b, the resilient material 1702 is removed. Accordingly, in some instances, the pliable film 1902 and/or interconnect layer 1092 are exposed from the backside of the device. The controller 604 remains attached to the pliable film 1902, and, in embodiments utilizing alignment structures 1602, the alignment structures 1602 remain attached as well. Referring to block 1416 of FIG. 14 and FIG. 21, ultrasound transducers 210 of the transducer array 602 are attached to the pliable film 1902 in the reserved area 1504 where the resilient material 1702 was removed. Soldering, chemical adhesion, and other methods may be used to fixedly attach the transducer 210. In an embodiment including alignment structures 1602, the alignment structures 1602 are used to guide the transducers 210 into place on the pliable film 1902. Referring to block 1418 of FIG. 14 and FIG. 22, remaining areas of attached substrate 1501 not associated with the controllers 604 are removed. From FIG. 23, it can be seen that the controllers 604, the transducers 210, the pliable film 1902, and the interconnect layer 1802 make up a scanner 110 in an unrolled form. Referring to block 1420, the unrolled scanner 110 is provided for rolling and final manufacturing.

Utilizing microassembly in fabricating the scanner 110 may improve yield, reduce manufacturing time, and/or allow scaling to smaller device widths. For example forming interconnects 1802 directly on the substrate allows manufacturers to use more precise substrate-based metallization processes such as those used in semiconductor manufacturing. This offers greater control over interconnect width, thickness, location, and pitch. Furthermore, by forming interconnects 1802 and the pliable film 1902 directly on the substrate 1501 used to manufacture the controllers, such methods of the present disclosure avoid introducing alignment issues when bonding elements to the flex circuit 606. Alignment issues impact yield, increase manufacturing complexity, and prevent utilizing smaller components. Additionally, embodiments utilizing alignment structures 1602 to place the transducers 210 alleviate another source of alignment problems. Moreover, forming interconnects 1802 directly on the controller 604 eliminates a solder junction that might otherwise present a potential yield loss and a point of failure.

Figure 24:
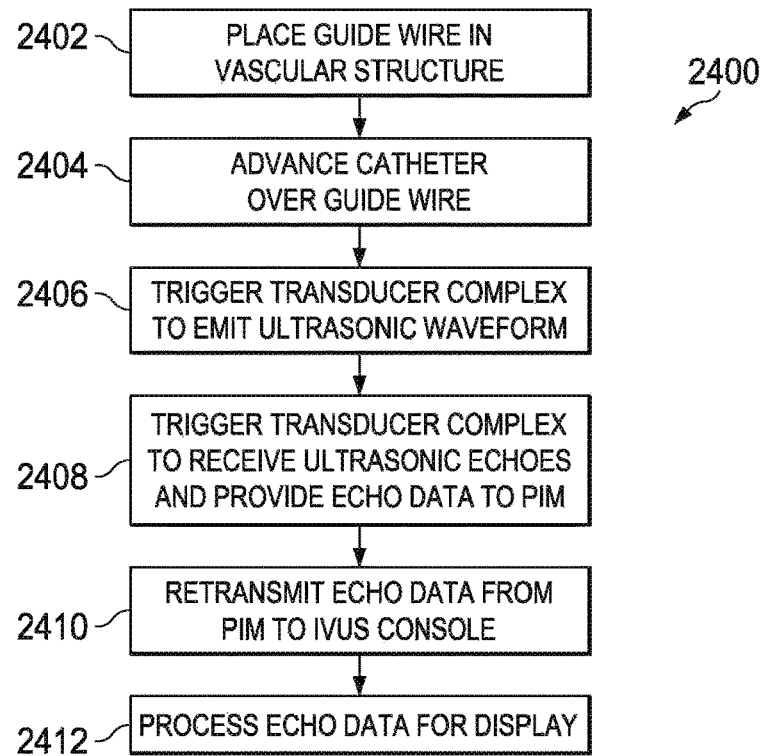
FIG. 24 is a flow diagram of a method of manufacturing an ultrasound scanner assembly according to an embodiment of the present disclosure.
Figure 25:
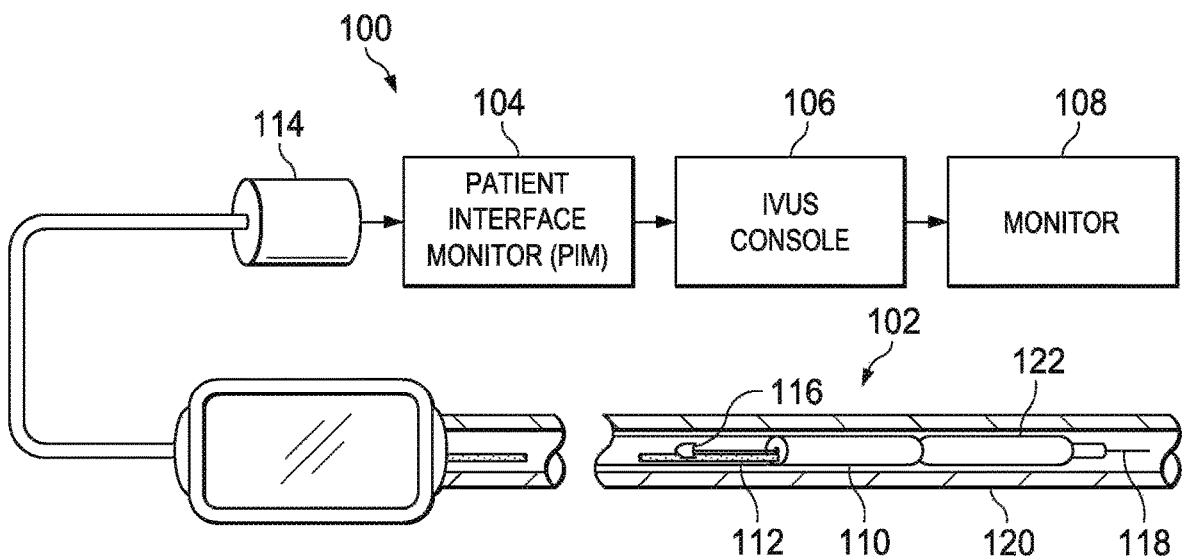
FIG. 25 is a flow diagram of a method of utilizing an IVUS catheter according to an embodiment of the present disclosure.

A method 2400 of utilizing an IVUS catheter 102 is disclosed with reference to FIGS. 24 and 25. FIG. 24 is a flow diagram of the method of utilizing the IVUS catheter 102 according to an embodiment of the present disclosure. It is understood that additional steps can be provided before, during, and after the steps of method 2400, and some of the steps described can be replaced or eliminated for other embodiments of the method. FIG. 25 is a diagrammatic schematic view of an IVUS system in operation according to an embodiment of the present disclosure.

Referring to block 2402 of FIG. 24 and FIG. 25, in an illustrative example of a typical environment and application of the system, a surgeon places a guide wire 118 in the vascular structure 120. The guide wire 118 is threaded through at least a portion of the distal end of the IVUS catheter 102 either before, during, or after placement of the guide wire 118. Referring to block 2404 of FIG. 24, once the guide wire 118 is in place, the IVUS catheter 102 is advanced over the guide wire. Referring to block 2406, the scanner 110 is activated. Signals sent from the PIM 104 to the scanner assembly 110 via the cable 112 cause transducers within the assembly 110 to emit a specified ultrasonic waveform. The ultrasonic waveform is reflected by the vascular structure 120. Referring to block 2408 of FIG. 24, the reflections are received by the transducers within the scanner assembly 110 and are amplified for transmission via the cable 112. The echo data is placed on the cable 112 and sent to the PIM 104. The PIM 104 amplifies the echo data and/or performs preliminary pre-processing, in some instances. Referring to block 2410 of FIG. 24, the PIM 104 retransmits the echo data to the IVUS console 106. Referring to block 2412 of FIG. 24, the IVUS console 106 aggregates and assembles the received echo data to create an image of the vascular structure 120 for display on the monitor 108. In some exemplary applications, the IVUS catheter is advanced beyond the area of the vascular structure 120 to be imaged and pulled back as the scanner 110 is operating, thereby exposing and imaging a longitudinal portion of the vascular structure 120. To ensure a constant velocity, a pullback mechanism is used in some instances. A typical withdraw velocity is 0.5 mm/s. In some embodiments, the device 102 includes an inflatable balloon portion 122. As part of a treatment procedure, the device may be positioned adjacent to a stenosis (narrow segment) or an obstructing plaque within the vascular structure 120 and inflated in an attempt to widen the restricted area of the vascular structure 120.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal device comprising:
an imaging assembly disposed on a distal portion of the intraluminal device and comprising a plurality of imaging elements;
a controller assembly in communication with the imaging assembly and disposed on the distal portion of the intraluminal device, the controller assembly comprising a primary controller and a plurality of secondary controllers in communication with the primary controller, wherein the primary controller and the plurality of secondary controllers are coupled to a flexible substrate positioned around the distal portion of the intraluminal device, wherein the primary controller and the plurality of secondary controllers are aligned around the distal portion of the intraluminal device, wherein each of the plurality of secondary controllers is electrically coupled to at least one other secondary controller via a plurality of lateral conductive traces, wherein each of the plurality of secondary controllers is electrically coupled to a respective subset of imaging elements via a plurality of longitudinal conductive traces, and wherein the primary controller is electrically coupled only to the plurality of secondary controllers via the plurality of lateral conductive traces; and
a cable directly coupled to the primary controller and comprising a differential pair of wires placing the primary controller in communication with an imaging system, the differential pair of wires are configured to transmit control data to the primary controller for activating a portion of the imaging elements and the primary controller engages at least one secondary controller to activate the portion of the imaging elements.

2. The intraluminal device of claim 1, wherein the cable further comprises a voltage wire configured to supply voltage to drive the imaging elements when activated.

3. The intraluminal device of claim 1, wherein the cable further comprises a ground wire.

4. The intraluminal device of claim 1, wherein the cable is directly coupled to a patient interface module of the imaging system.

5. The intraluminal device of claim 1, wherein the differential pair of wires is further configured to transmit a voltage to drive circuitry of the controller assembly.

6. The intraluminal device of claim 1, wherein the control data transmitted to the primary controller comprises commands for the primary controller that are selected from the group consisting of: designating transmit and receive imaging elements, designating a type of waveform emitted from the imaging elements, and a combination thereof.

7. The intraluminal device of claim 1, wherein the plurality of imaging elements is arranged at least partially around a longitudinal axis of the intraluminal device.

8. The intraluminal device of claim 1, wherein the primary controller comprises a drive amplifier.

9. The intraluminal device of claim 1, wherein the primary controller, secondary controllers, or both comprise 8-channel controllers.

10. The intraluminal device of claim 1, wherein the imaging assembly and the controller assembly are formed on a flexible circuit.

11. The intraluminal device of claim 10, wherein the flexible circuit is wrapped around at least part of the distal portion of the intraluminal device.

12. The intraluminal device of claim 1, wherein the imaging elements comprise ultrasound transducers.

13. An imaging core assembly for an intraluminal device, the imaging core assembly comprising:
a flexible circuit configured to transition from a flat configuration to a rolled configuration;
a plurality of imaging elements disposed on the flexible circuit and configured to form an annular configuration when the flexible circuit is in the rolled configuration;

a controller assembly in communication with the plurality of imaging elements and disposed on the flexible circuit, the controller assembly comprising a primary controller and a plurality of secondary controllers in communication with the primary controller, wherein the primary controller and the plurality of secondary controllers are coupled to a flexible substrate positioned around a distal portion of the intraluminal device, wherein the primary controller and the plurality of secondary controllers are aligned around the distal portion of the intraluminal device, wherein each of the plurality of secondary controllers is electrically coupled to at least one other secondary controller via a plurality of lateral conductive traces, wherein each of the plurality of secondary controllers is electrically coupled to a respective subset of imaging elements via a plurality of longitudinal conductive traces, and wherein the primary controller is electrically coupled only to the plurality of secondary controllers via the plurality of lateral conductive traces; and a cable directly coupled to the primary controller and comprising a differential pair of wires placing the primary controller in communication with an imaging system; wherein the differential pair of wires are configured to transmit control data to the primary controller for activating a portion of the imaging elements and the primary controller engages at least one secondary controller to activate the portion of the imaging elements.

14. The imaging core assembly of claim 13, wherein the cable further comprises a voltage wire configured to supply voltage to drive the imaging elements when activated.

15. The imaging core assembly of claim 13, wherein the cable further comprises a ground wire.

16. The imaging core assembly of claim 13, wherein the cable is directly coupled to a patient interface module of the imaging system.

17. The imaging core assembly of claim 13, wherein the differential pair of wires is further configured to transmit a voltage to drive circuitry of the controller assembly.

18. The imaging core assembly of claim 13, wherein the control data transmitted to the primary controller comprises commands for the primary controller that are selected from the group consisting of: designating transmit and receive imaging elements, designating a type of waveform emitted from the imaging elements, and a combination thereof.

19. The intraluminal device of claim 1, wherein the controller assembly comprises at least eight controllers, and wherein the primary controller and the plurality of secondary controllers are arranged in a polygon configuration of at least eight sides around the distal portion of the intraluminal device.

20. The intraluminal device of claim 19, wherein the polygon configuration is a nonagon configuration.

* * * * *